US006685708B2

(12) United States Patent  
Monassevitch et al.

(10) Patent No.: US 6,685,708 B2
(45) Date of Patent: Feb. 3, 2004

(54) STAPLES FOR BONE FIXATION

(75) Inventors: Leonid Monassevitch, Hadera (IL); Michael Arad, Tel Aviv (IL); Zvi Laster, Poriya Ilit (IL)

(73) Assignee: NiTi Alloys Technologies Ltd., Netanya (IL)

( * ) Notice: Subject to any disclaimer, the term of this patent is extended or adjusted under 35 U.S.C. 154(b) by 281 days.

(21) Appl. No.: 09/795,253

(22) Filed: Feb. 28, 2001

(65) Prior Publication Data

US 2002/0029044 A1 Mar. 7, 2002

(30) Foreign Application Priority Data

Sep. 7, 2000 (IL) ................................................. 138320

(51) Int. Cl.[7] .............................................. A61B 17/84
(52) U.S. Cl. ........................................... 606/75; 606/72
(58) Field of Search ........................... 606/75, 78, 207, 606/219; 411/909; 254/28

(56) References Cited

U.S. PATENT DOCUMENTS

| | | | |
|---|---|---|---|
| 1,422,538 A | * | 7/1922 | Cameron |
| 4,485,816 A | * | 12/1984 | Krumme |
| 4,526,174 A | * | 7/1985 | Froehlich |
| 4,665,906 A | | 5/1987 | Jervis |
| 4,841,960 A | | 6/1989 | Garner |
| 5,044,540 A | * | 9/1991 | Dulebohn |
| 5,171,252 A | * | 12/1992 | Friedland |
| 5,246,443 A | * | 9/1993 | Mai ............................ 606/78 |
| 5,366,479 A | * | 11/1994 | McGarry et al. ............ 606/219 |
| 5,660,188 A | * | 8/1997 | Groiso |
| 6,325,805 B1 | * | 12/2001 | Ogilvie et al. ................ 606/75 |

FOREIGN PATENT DOCUMENTS

WO       WO 99/16385      *  4/1999

OTHER PUBLICATIONS

"Use of TiNiCo Shape–Memory Clamps in the Surgical Treatment of Mandibular Fractures", Jan Drugacz, MD, Zdzislaw Lekston, PhD, Henryk Morawiec and Krzysztof Januszewski, MD, pp 665–672, J Oral Maxilofac Surg 53, 1995.

"Using Nitinol Alloys", Hodgson & Brown, company promotional material from Third International Conference on Shape Memory and Superelastic Technologies, 2000, of Shape Memory Applications, Inc., 1070 Commercial Street, Suite #110, San Jose, CA 95112, USA www.sma–inc.com., pp. 1, 1, 5, 6 (2000).

"Nitinol Technology", company promotional material from internet site of NDC, Nitinol Devices & Components, 47533 Westinghouse Drive, Fremont, CA 94539, Tel: 510–623–6996, Fax: 510–623–6995, www.nitinol.com., pp. 1, 1–3, (Jan. 17, 2001).

* cited by examiner

Primary Examiner—Ralph A. Lewis
(74) Attorney, Agent, or Firm—Pearne & Gordon LLP

(57) ABSTRACT

Apparatus for increasing the span length of a bone staple, which includes two prongs connected by a system which provides a mechanical advantage to facilitate bringing the prongs closer together or further apart. One prong includes a staple receptor. The other prong includes a cam-like head such that when the prongs are brought together the staple span length of a staple in the receptor increases. Alternatively, the two prongs are disposed for mounting a staple. When the prongs are pushed apart the staple span length increases. The present invention also relates to a bone staple formed of a shape-memory alloy and an apparatus associated with the staple. The apparatus deforms the staple by increasing its span length and facilitating its insertion into bone tissue. The deformation range of the staple allows the staple to revert to its original shape when the temperature is changed.

27 Claims, 18 Drawing Sheets

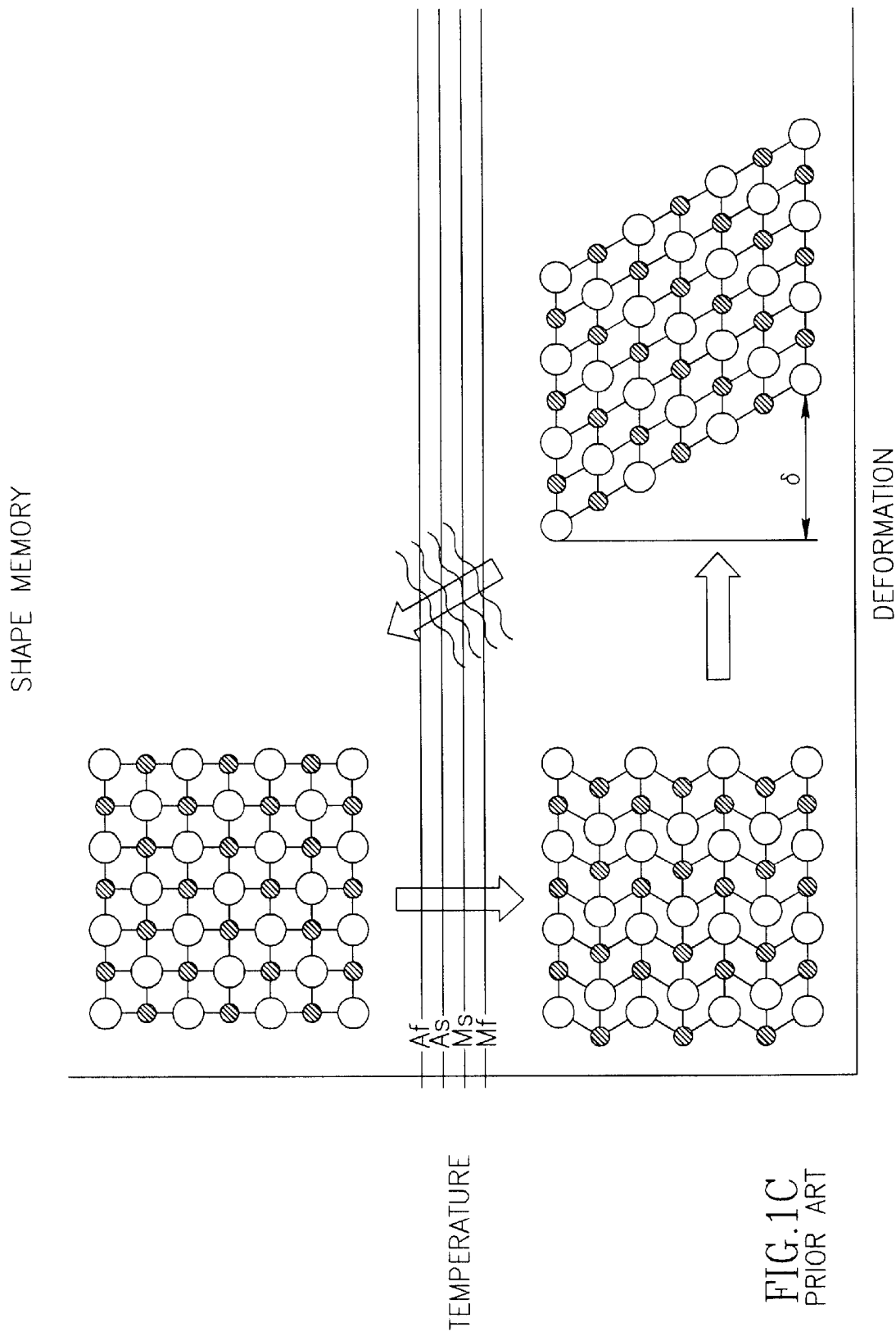

| α° \ δ | R1/t | | | | |
|---|---|---|---|---|---|
| | 4% | 5% | 6% | 7% | 8% |
| 95 | 0.18 | 0.05 | – | – | – |
| 100 | 0.80 | 0.55 | 0.38 | 0.26 | 0.18 |
| 105 | 1.36 | 1.00 | 0.76 | 0.59 | 0.46 |
| 110 | 1.86 | 1.41 | 1.11 | 0.89 | 0.73 |
| 115 | 2.33 | 1.78 | 1.42 | 1.16 | 0.97 |
| 120 | 2.75 | 2.13 | 1.71 | 1.41 | 1.19 |
| 125 | 3.14 | 2.44 | 1.97 | 1.64 | 1.39 |
| 130 | 3.50 | 2.73 | 2.22 | 1.85 | 1.58 |
| 135 | 3.83 | 3.00 | 2.44 | 2.05 | 1.75 |
| 140 | 4.14 | 3.25 | 2.65 | 2.23 | 1.91 |
| 145 | 4.43 | 3.48 | 2.85 | 2.40 | 2.06 |
| 150 | 4.70 | 3.70 | 3.03 | 2.56 | 2.20 |
| 155 | 4.95 | 3.90 | 3.20 | 2.71 | 2.33 |
| 160 | 5.19 | 4.09 | 3.36 | 2.84 | 2.45 |
| 165 | 5.41 | 4.27 | 3.52 | 2.97 | 2.57 |
| 170 | 5.62 | 4.44 | 3.66 | 3.10 | 2.68 |
| 175 | 5.81 | 4.60 | 3.79 | 3.21 | 2.78 |
| 180 | 6.00 | 4.75 | 3.92 | 3.32 | 2.88 |
| 185 | 6.18 | 4.89 | 4.04 | 3.42 | 2.97 |
| 190 | 6.34 | 5.03 | 4.15 | 3.52 | 3.05 |
| 195 | 6.50 | 5.15 | 4.26 | 3.62 | 3.13 |
| 200 | 6.65 | 5.28 | 4.36 | 3.70 | 3.21 |
| 205 | 6.79 | 5.39 | 4.46 | 3.79 | 3.29 |
| 210 | 6.93 | 5.50 | 4.55 | 3.87 | 3.36 |
| 215 | 7.06 | 5.60 | 4.64 | 3.94 | 3.42 |
| 220 | 7.18 | 5.70 | 4.72 | 4.02 | 3.49 |
| 225 | 7.30 | 5.80 | 4.80 | 4.09 | 3.55 |
| 230 | 7.41 | 5.89 | 4.88 | 4.15 | 3.61 |
| 235 | 7.52 | 5.98 | 4.95 | 4.22 | 3.66 |
| 240 | 7.63 | 6.06 | 5.02 | 4.28 | 3.72 |
| 245 | 7.72 | 6.14 | 5.09 | 4.34 | 3.77 |
| 250 | 7.82 | 6.22 | 5.15 | 4.39 | 3.82 |

FIG.9A

| α° \ δ | R1/t | | | | | |
|---|---|---|---|---|---|---|
| | 9% | 10% | 11% | 12% | 13% | 14% |
| 95 | – | – | – | – | – | – |
| 100 | 0.11 | 0.05 | 0.00 | – | – | – |
| 105 | 0.37 | 0.29 | 0.22 | 0.17 | 0.12 | 0.08 |
| 110 | 0.60 | 0.50 | 0.42 | 0.35 | 0.29 | 0.24 |
| 115 | 0.82 | 0.70 | 0.60 | 0.51 | 0.44 | 0.39 |
| 120 | 1.01 | 0.88 | 0.76 | 0.67 | 0.59 | 0.52 |
| 125 | 1.20 | 1.04 | 0.91 | 0.81 | 0.72 | 0.64 |
| 130 | 1.36 | 1.19 | 1.05 | 0.94 | 0.84 | 0.75 |
| 135 | 1.52 | 1.33 | 1.18 | 1.06 | 0.95 | 0.86 |
| 140 | 1.66 | 1.46 | 1.30 | 1.17 | 1.05 | 0.95 |
| 145 | 1.80 | 1.59 | 1.41 | 1.27 | 1.15 | 1.04 |
| 150 | 1.92 | 1.70 | 1.52 | 1.37 | 1.24 | 1.13 |
| 155 | 2.04 | 1.81 | 1.62 | 1.46 | 1.32 | 1.21 |
| 160 | 2.15 | 1.91 | 1.71 | 1.54 | 1.40 | 1.28 |
| 165 | 2.25 | 2.00 | 1.79 | 1.62 | 1.48 | 1.35 |
| 170 | 2.35 | 2.09 | 1.87 | 1.70 | 1.55 | 1.42 |
| 175 | 2.44 | 2.17 | 1.95 | 1.77 | 1.61 | 1.48 |
| 180 | 2.53 | 2.25 | 2.02 | 1.83 | 1.67 | 1.54 |
| 185 | 2.61 | 2.32 | 2.09 | 1.90 | 1.73 | 1.59 |
| 190 | 2.69 | 2.39 | 2.16 | 1.96 | 1.79 | 1.64 |
| 195 | 2.76 | 2.46 | 2.22 | 2.01 | 1.84 | 1.69 |
| 200 | 2.83 | 2.53 | 2.28 | 2.07 | 1.89 | 1.74 |
| 205 | 2.90 | 2.59 | 2.33 | 2.12 | 1.94 | 1.78 |
| 210 | 2.96 | 2.64 | 2.38 | 2.17 | 1.98 | 1.83 |
| 215 | 3.02 | 2.70 | 2.43 | 2.21 | 2.03 | 1.87 |
| 220 | 3.08 | 2.75 | 2.48 | 2.26 | 2.07 | 1.91 |
| 225 | 3.13 | 2.80 | 2.53 | 2.30 | 2.11 | 1.94 |
| 230 | 3.19 | 2.85 | 2.57 | 2.34 | 2.15 | 1.98 |
| 235 | 3.24 | 2.89 | 2.61 | 2.38 | 2.18 | 2.01 |
| 240 | 3.28 | 2.94 | 2.65 | 2.42 | 2.22 | 2.04 |
| 245 | 3.33 | 2.98 | 2.69 | 2.45 | 2.25 | 2.08 |
| 250 | 3.38 | 3.02 | 2.73 | 2.49 | 2.28 | 2.11 |

FIG.9B

| α° \ δ | R1/t | | | | | |
|---|---|---|---|---|---|---|
| | 15% | 16% | 17% | 18% | 19% | 20% |
| 95 | – | – | – | – | – | – |
| 100 | – | – | – | – | – | – |
| 105 | 0.05 | 0.02 | – | – | – | – |
| 110 | 0.20 | 0.16 | 0.13 | 0.10 | 0.07 | 0.05 |
| 115 | 0.33 | 0.29 | 0.25 | 0.21 | 0.18 | 0.15 |
| 120 | 0.46 | 0.41 | 0.36 | 0.32 | 0.28 | 0.25 |
| 125 | 0.57 | 0.52 | 0.46 | 0.42 | 0.38 | 0.34 |
| 130 | 0.68 | 0.62 | 0.56 | 0.51 | 0.46 | 0.42 |
| 135 | 0.78 | 0.71 | 0.65 | 0.59 | 0.54 | 0.50 |
| 140 | 0.87 | 0.79 | 0.73 | 0.67 | 0.62 | 0.57 |
| 145 | 0.95 | 0.88 | 0.81 | 0.74 | 0.69 | 0.64 |
| 150 | 1.03 | 0.95 | 0.88 | 0.81 | 0.75 | 0.70 |
| 155 | 1.11 | 1.02 | 0.94 | 0.87 | 0.81 | 0.76 |
| 160 | 1.18 | 1.09 | 1.01 | 0.93 | 0.87 | 0.81 |
| 165 | 1.24 | 1.15 | 1.06 | 0.99 | 0.92 | 0.86 |
| 170 | 1.30 | 1.21 | 1.12 | 1.04 | 0.97 | 0.91 |
| 175 | 1.36 | 1.26 | 1.17 | 1.09 | 1.02 | 0.96 |
| 180 | 1.42 | 1.31 | 1.22 | 1.14 | 1.07 | 1.00 |
| 185 | 1.47 | 1.36 | 1.27 | 1.18 | 1.11 | 1.04 |
| 190 | 1.52 | 1.41 | 1.31 | 1.23 | 1.15 | 1.08 |
| 195 | 1.56 | 1.45 | 1.35 | 1.26 | 1.19 | 1.12 |
| 200 | 1.61 | 1.49 | 1.39 | 1.30 | 1.22 | 1.15 |
| 205 | 1.65 | 1.53 | 1.43 | 1.34 | 1.26 | 1.18 |
| 210 | 1.69 | 1.57 | 1.47 | 1.37 | 1.29 | 1.21 |
| 215 | 1.73 | 1.61 | 1.50 | 1.41 | 1.32 | 1.24 |
| 220 | 1.77 | 1.64 | 1.53 | 1.44 | 1.35 | 1.27 |
| 225 | 1.80 | 1.68 | 1.56 | 1.47 | 1.38 | 1.30 |
| 230 | 1.83 | 1.71 | 1.59 | 1.50 | 1.41 | 1.33 |
| 235 | 1.87 | 1.74 | 1.62 | 1.52 | 1.43 | 1.35 |
| 240 | 1.90 | 1.77 | 1.65 | 1.55 | 1.46 | 1.38 |
| 245 | 1.93 | 1.79 | 1.68 | 1.57 | 1.48 | 1.40 |
| 250 | 1.95 | 1.82 | 1.70 | 1.60 | 1.50 | 1.42 |

FIG.9C

STAPLES FOR BONE FIXATION

FIELD OF THE INVENTION

The present invention relates generally to staples for bone fixation, formed of shape-memory-alloys (SMA) and other biocompatible metals and alloys. The present invention relates in particular to SMA staples of adjustable length spans.

BACKGROUND OF THE INVENTION

Titanium-nickel, shape-memory alloys are biocompatible and resistant to corrosion; therefore, they are suitable for medical applications. These alloys have different phase structures, hence, different mechanical properties, at different temperatures. Information about shape memory alloys may be found, for example, on web site www.nitinol.com, by Nitinol Devices & components, copyright 1998, and in Conference information of "The Third International conference on Shape Memory and Superelastic Technologies Engineering and Biomedical Applications," held in Pacific Grove, Calif. during Apr. 30–May 4, 2000.

FIGS. 1A and 1B, together, schematically illustrate a typical temperature hysteresis, typical elastic stresses, es, in phase transitions, and typical stress-strain curves for a shape-memory alloy in the austenitic and martensitic phases. At a low temperature, the alloy is martensitic, and is soft and plastic, having a low es. At a high temperature, the alloy is austenitic and tough, having a high es. When a martensitic alloy is heated to a temperature $A_s$, the austenitic phase begins to form. Above a temperature $A_f$, the alloy is fully austenitic. Likewise, as an austenitic alloy is cooled to a temperature $M_s$, the martensitic phase begins to form. Below a temperature $M_f$, the alloy is fully martensitic.

The temperature-dependent phase structure gives rise to shape memory. At the fully austenitic phase, under proper heat treatment and working conditions, an SMA element can be given a physical shape and "pre-programmed" to memorize that shape and resume it, whenever in the austenitic phase. The "memorized" SMA element may then be cooled to a martensitic phase and plastically deformed in the martensitic phase. But when heated back to the austenitic phase is will resume its memorized shape. The transformation temperature between the phases is noted as TTR.

The reason for the shape memory is found in the phase structure of the alloy. Most metals deform by atomic slip. Dislocations and atomic planes slide over one another and assume a new crystal position. In the new position, the crystal has no memory of its order prior to the deformation. With increased deformation, there is generally a work-hardening effect, in which the increased tangle of dislocations makes additional deformation more difficult. This is the case even when the increased deformation is in the direction of restoring the crystal to its original shape. However, for shape memory alloys, both transitions between the austenitic and martensitic phases and deformation in the martensitic phase change lattice angles in the crystal, uniformly for the whole crystal. The original austenitic lattice structure is "remembered" and can be restored.

FIG. 1C schematically illustrates typical phase structures of a shape-memory alloy, as functions of temperature and deformation, as follows:

in the austenitic phase, the crystal has a cubic structure, and the atoms in the lattice are arranged generally at right angles to each other;

when the austenitic crystal is cooled to a martensitic phase, a twinned lattice structure is formed;

when the twinned martensitic crystal is deformed by an amount no greater than δ, the twinned structure is "stretched" so that the atoms in the lattice are arranged generally at oblique angles to each other, wherein the oblique angles are determined by the amount of deformation; and when the deformed martensitic crystal is heated, the crystal resumes its cubic structure, wherein, again, the atoms in the lattice are arranged generally at right angles to each other.

Another property that can be imparted to SMA elements, under proper heat treatment and working conditions, is super-elasticity, or Stress-Induced Martensite (SIM). With this property, a fully austenitic SMA element, at a temperature above $A_f$, will become martensitic and plastic under high stress, and deform under the stress. When the stress is removed, the SMA element will return to the austenitic phase and to its memorized shape in the austenitic phase. Super-elasticity is also referred to as rubber-band like property, because the SMA element behaves like a rubber band or a spring, deforming under stress and resuming its original shape when the stress is removed. However, this property is present only above the temperature $A_f$, and only when it is specifically imparted to an SMA element, by proper heat treatment and working conditions.

FIG. 1D schematically illustrates a typical cyclic transformation of a super elastic alloy, at a constant temperature above the temperature $A_f$. The transformation between the austenitic phase and a stress-induced martensitic phase is brought about by stress and is eliminated when the stress is removed.

It should be emphasized that both full shape memory and stress-induced superelasticity occur as long as the deformation is no greater than δ, and with greater deformations the crystal structure will be damaged.

Staples and clamps for bone fixation of fractures, formed of shape-memory alloys, are known. They are easily inserted in a martensitic phase, when deformed to an open, straight-edge state, and they resume a closed, clamped state in the body, thus forming a closure on the fracture.

Basically, there are two approaches to working with SMA elements for bone fixation. In accordance with the first approach, the elements are fully martensitic at room temperature and are deformed and inserted into the bone when at room temperature. After insertion, the elements are locally heated to about 42–45° C., a temperature above $A_f$, and transform to the austenitic shape, resuming their memorized austenitic shape. The staples then cool down to body temperature, which is generally below $A_f$, although still above $M_s$. Thus, in the body, the SMA elements remain austenitic and retain their austenitic shape. The advantage of this approach is that the SMA elements need not be cooled in order to remain in the martensitic phase, prior to insertion. The disadvantages, however, are that the mechanical properties of the SMA elements are not uniquely defined at body temperature, and that the SMA elements are not super-elastic in the body.

In accordance with the second approach, $A_f$ is designed below body temperature. The SMA elements are cooled to 0–5° C., or lower, to a temperature below their $M_f$ temperature, for deformation and insertion into the bone. Upon insertion, the elements are naturally heated to body temperature, by contact with the body only. Since body temperature is above $A_f$, the elements transform to the austenitic phase and resume their memorized austenitic shape. The advantages of this approach are that, in the body, the SMA elements are fully austenitic, their mechanical properties are defined, and if properly heat-treated, they are super-elastic. The disadvantage, however, is that plastic deformation in the martensitic phase must be performed after the elements are cooled, and the deformed SMA elements must remain cooled during procedure manipulation and insertion.

The publication, "Use of TiNiCo Shape-Memory Clamps in the Surgical Treatment of Mandibular Fractures," by Drugacz J., et al., American Association of Oral and Maxillofacial Surgeons, 0278-2391/95/5306-0006, describes a study in which clamps made of $Ti_{50}Ni_{48.7}Co_{1.3}$, memorized to resume their shape at body temperature, were used to fix mandibular fractures. Seventy-seven patients with mandibular single or multiple fractures were treated, using 124 clamps. In 72 of the 75 patients, the treatment progressed satisfactorily, and only in five cases, infections occurred. The study concluded that the application of shape-memory clamps for surgical treatment of mandibular fractures facilitated treatment and ensured stable fixation of the bone fragments. There was no observation of pathologic tissue reaction to the clamps.

SMA staples are commercially avialable from MEMO-METAL Industries, of Cedex, France, as well as from Medical Engineering Center, Siberian Physics & Technical Institute, Tomsk, Russia, and from DePuy International Ltd., a Johnson & Johnson company, in Leeds, England, and DePuy France S.A., Cedex, France, as well as from other companies. Generally a range of shapes and sizes are offered by each company.

U.S. Pat. No. 4,665,906 to Jervis describes medical devices that incorporate stress-induced martensite alloy elements. Generally, the steps involved in the use of these devices are:

deforming a medical device into a deformed shape different from a final shape, by the formation of stress-induced martensite;

restraining the deformed shape by the application of a restraining means;

positioning the medical device and restraining means within, or in proximity to, the body;

removing the restraining means;

isothermally transforming the device from the deformed shape into the final shape.

Methods and apparatus for adjusting the length spans of bone staples are known. For example, U.S. Pat. No. 4,841, 960 to Garner describes a staple whose web, or central portion, can be crimped by a pliers-like crimping device, thus shortening its length. However, this method is inappropriate for SMA elements, since the deformation will not be maintained in the austenitic shape, in the body; rather, the SMA elements will resume their memorized shape.

SUMMARY OF THE INVENTION

It is an aim of the present invention to provide apparatus and method for adjusting the length spans of SMA staples for bone fixations, prior to their insertion into the bone.

There is thus provided, in accordance with the present invention, apparatus for increasing a length span of a staple, which includes:

proximal and distal ends with respect to a user, which define a z-axis of an x;y;z coordinate system between them; and first and second prongs, joined by a system which provides a mechanical advantage to selectably bringing said first and second prongs together and pushing them apart, wherein said first prong further includes, at said distal end, a staple receptor, with a channel, for mounting said staple thereon, said channel defining an x-axis of the x;y;z coordinate system, parallel to said staple length span, and perpendicular to the direction of bringing first and second prongs together and pushing them apart, wherein said second prong further includes, at said distal end, a thin, cam-like head, having a width span that increases in the direction of increasing y, operable to increase said staple length span, and wherein, as said first and second prongs are brought together, said thin, cam-like head is arranged to slide between said staple receptor and said staple, mounted thereon, so as to wedge between said staple receptor and said staple and increase the length span of said staple.

Further in accordance with the present invention, said apparatus includes a mechanical stopping component, for controlling the amount by which said first and second prongs are brought together, hence, the length-span increase to said staple.

Additionally, in accordance with the present invention, said apparatus includes a gauge, for measuring the amount by which said first and second prongs are brought together, hence, the length-span increase to said staple.

Further in accordance with the present invention, said system which provides a mechanical advantage to selectably bringing said first and second prongs together and pushing them apart is a swivel pin.

Alternatively, said system which provides a mechanical advantage to selectably bringing said first and second prongs together and pushing them apart is a threaded bolt.

Alternatively, said system which provides a mechanical advantage to selectably bringing said first and second prongs together and pushing them apart is a pulley.

Further in accordance with the present invention, said staple is formed of an SMA alloy.

Additionally, in accordance with the present invention, said staple has an initial length span of 6 mm, wherein said apparatus is arranged for increasing said length span to a value between 6 and 10 mm.

Alternatively, said staple has an initial length span of 10 mm, wherein said apparatus is arranged for increasing said length span to a value between 10 and 14 mm.

Alternatively, said staple has an initial length span of 14 mm, wherein said apparatus is arranged for increasing said length span to a value between 14 and 18 mm.

Alternatively, said staple has an initial length span between 3 and 100 mm, wherein said apparatus is arranged for increasing said length span by an amount between 0 and 10 mm.

There is thus provided, in accordance with an alternative embodiment of the present invention, apparatus for increasing a length span of a staple, which includes:

proximal and distal ends with respect to a user; and first and second prongs, joined by a system which provides a mechanical advantage to selectably bringing said first and second prongs together and pushing them apart, wherein said first and second prongs further include, at said distal end, tips, arranged for mounting said staple thereon, when said prongs are brought together, and wherein, as said first and second prongs are pushed apart, said tips pry said staple, mounted thereon, wider, thus increasing the length span of said staple.

There is thus also provided, in accordance with the present invention, a method of increasing a length span of a staple, which includes the steps of:

employing prongs which define a z-axis of an x;y;z coordinate system, generally parallel with their longitudinal axis;

mounting the staple on a staple receptor, which is arranged on the first prong, and which defines an x-axis of the x;y;z coordinate system, parallel with a length direction of the staple; and sliding a thin cam, arranged on a second prong, and having a width which increases in the direction of increasing y, between the staple receptor and the staple mounted thereon, thus wedging the thin cam between the staple receptor and the staple; and plastically deforming the staple, to increase its length span.

Further in accordance with the present invention, said step of sliding a thin cam further includes sliding by a predetermined amount, thus predetermining the length-span increase of the staple.

Additionally, in accordance with the present invention, the staple is formed of a shape-memory alloy having a fully martensitic phase within a first temperature range, and having a fully austenitic phase within a second temperature range, which is higher than the first temperature range, wherein said step of plastically deforming the staple includes plastically deforming the staple by reversible martensitic deformation.

Further in accordance with the present invention, said step of plastically deforming the staple by reversible martensitic deformation includes plastically deforming the staple at a temperature range of the fully martensitic phase.

Alternatively, said step of plastically deforming the staple by reversible martensitic deformation includes plastically deforming the staple in a stress-induced martensitic phase at a temperature range of the fully austenitic phase.

There is thus also provided, in accordance with the present invention, a method of bone fixation with an SMA staple, which includes the steps of:

drilling at least one pair of bores across a fracture interface of a bone;

measuring the distance span between the two bores of the bore pair;

selecting an SMA staple having a length span which is smaller than the distance span;

plastically deforming the staple, to increase its length span;

inserting the staple into the bores; and employing the staple in the plastically deformed state, which resulted from the length-span increase.

There is thus also provided, in accordance with the present invention, a method of increasing a length span of a staple, which includes the steps of:

mounting the staple on two tips that are arranged for receiving the staple when they are brought together; and plastically deforming the staple by prying the tips apart, to increase the length span of the staple.

Additionally, said step of plastically deforming the staple by prying the tips apart further includes prying by a predetermined amount.

There is thus also provided, in accordance with the present invention, a staple for bone fixation, formed of a shape-memory alloy having a fully martensitic phase within a first temperature range, and having a fully austenitic phase within a second temperature range, which is higher than the first temperature range, which includes:

a web having a first length span and a thickness;

two bending points, forming the end points of said web; and two semicircular end sections, beginning from said bending points, having a radius of curvature, an angle of curvature that is greater than 90°, and a thickness which is substantially the same as said web thickness, wherein by plastically deforming said staple, reversibly, in the fully martensitic phase, to decrease said angle of curvature to 90°, said semicircular end sections are straightened, to facilitate insertion into the bone, and said length span may be increased to a desired value, and wherein upon transformation to its austenitic shape, said staple generally resumes its original shape, but with a second length span that is greater than said first length span.

There is thus also provided, in accordance with the present invention, a method of bone fixation, which includes the steps of:

drilling at least one pair of bores across a fracture interface of a bone;

measuring the distance span between the two bores of the bore pair;

employing a staple for bone fixation, formed of a shape-memory alloy having a fully martensitic phase within a first temperature range, and having a rally austenitic phase within a second temperature range, which is higher than the first temperature range, which includes:
a web having a length span; and
two semicircular end sections, having angles of curvature that are greater than 90°;

plastically deforming the staple, reversibly, in its martensitic phase, to simultaneously decrease said angle of curvature to 90°, thus straightening the semicircular end sections, to facilitate insertion into the bone, and to increase the length span of the web to a desired value;

inserting the staple into the bores; and employing the staple in the plastically deformed state, which resulted from the length-span increase.

Additionally, in accordance with the present invention, said step of plastically deforming the staple, reversibly, in its martensitic phase, includes plastically deforming the staple at a temperature range of the fully martensitic phase.

Alternatively, said step of plastically deforming the staple, reversibly, in its martensitic phase, includes plastically deforming the staple in a stress-induced martensitic phase at a temperature range of the fully austenitic phase.

Further in accordance with the present invention, said method further includes plastically deforming the staple to increase the length span to a value which is substantially the same value as the distance span between the two bores of the bore pair.

Additionally, in accordance with the present invention, said step of plastically deforming includes plastically deforming to a strain that is less than 15%.

There is thus also provided, in accordance with the present invention, a method of bone fixation, which includes the steps of:

drilling at least one pair of bores across a fracture interface of a bone;

measuring the distance span between the two bores of the bore pair;

employing a staple for bone fixation, formed of a shape-memory alloy having a fully martensitic phase within a first temperature range, and having a fully austenitic phase within a second temperature range, which is higher than the first temperature range, which includes:
a web having a length span; and
two semicircular end sections, having angles of curvature that are greater than 90°;
plastically deforming the staple, reversibly, in its martensitic phase, to simultaneously decrease said angle of curvature to 90°, thus straightening the semicircular end sections, to facilitate insertion into the bone, and to increase the length span of the web to a desired value;
inserting the staple into the bores; and
employing the staple in a partially plastically deformed state, resulting from the length-span increase.

There is thus also provided, in accordance with the present invention, a staple for bone fixation which includes:
a web having:
a length span;
a curvature; and
a thickness,
wherein said staple may be plastically deformed by straightening its curvature, to increase its length span, and wherein the staple is employed in its plastically deformed state.
Additionally, said web includes more than one curvature.

BRIEF DESCRIPTION OF THE DRAWINGS

The present invention will be more clearly understood from the accompanying detailed description and drawings, in which same number designations are maintained throughout the figures for similar elements and in which:

FIG. 1C schematically illustrates typical phase structures of a shape-memory alloy, as functions of temperature and deformation, in accordance with the prior art;

FIGS. 9A–9C illustrate, in a table format, the percentage of plastic deformation that is encountered when the curvature of an element is varied, for the staple of FIG. 8;

DETAILED DESCRIPTION OF PREFERRED EMBODIMENTS

Figure 2A:
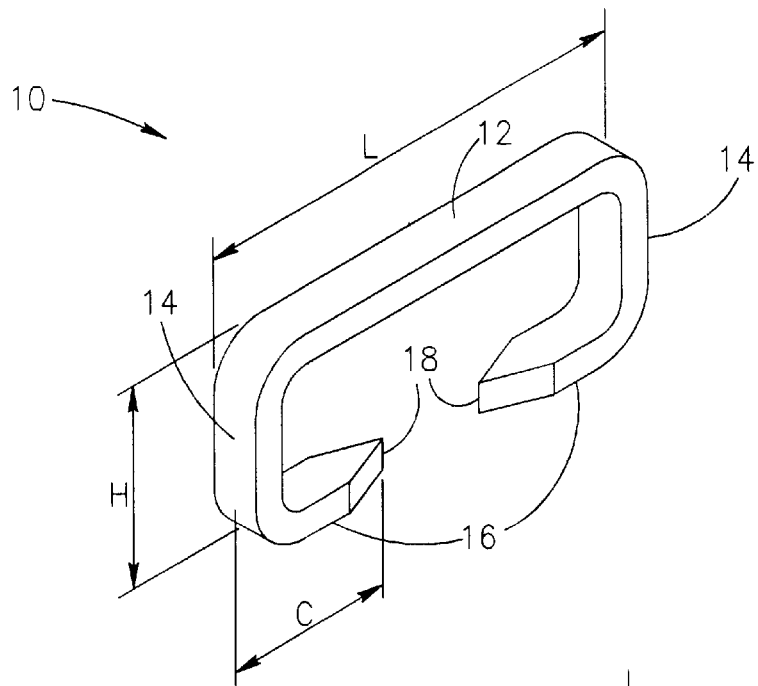
FIGS. 2A–2C schematically illustrate staples for bone fixation, in accordance with the present invention.

Reference is now made to FIG. 2A, which schematically illustrates a staple 10, in accordance with an embodiment of the present invention. Staple 10 includes a web 12, legs 14, clamping portions 16, and pointed edges 18. Preferably, staple 10 is used for bone fixation, for example of the maxillofacial or mandibular jawbones or of the hand, the foot, or the skull. However, staple 10 may be used for bone fixation of other bones as well. Preferably, staple 10 is formed of titanium-nickel, shape-memory alloy and is seen in FIG. 2A in an austenitic phase, depicting its memorized shape.

Staple 10 may have a length span L from as low as 4 mm to as high as 80 or 100 mm, depending on its application. In accordance with a preferred embodiment of the present invention, length span L is between 4 and 25 mm, and preferably between 6 and 18 mm. Preferably, legs 14 are formed at right angles to web 12 and clamping portions 16 are formed at right angles to legs 14, parallel to web 12.

Figure 2B:
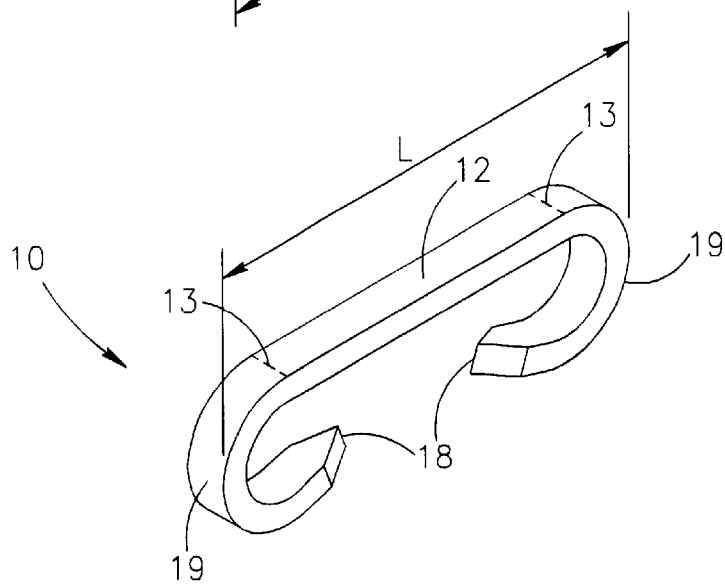
Figure 2C:
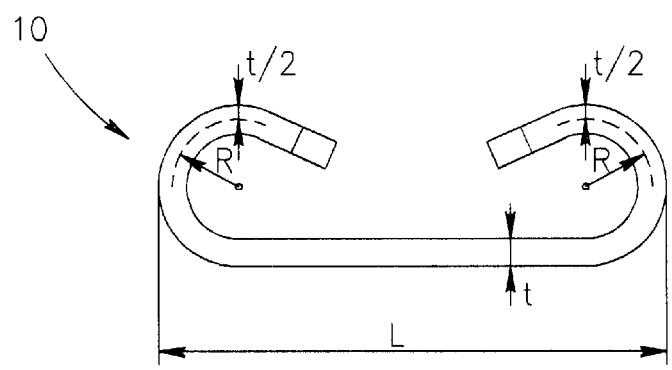

Reference is now made to FIGS. 2B and 2C, which schematically illustrate staple 10, in accordance with an alternative embodiment of the present invention. In accordance with the present embodiment, in its austenitic phase, staple 10 is formed of web 12 of length L, a thickness t, and two semicircular end sections 19, having a radius of curvature, R, measured as an inner radius plus half the thickness t. The cross-section of staple 10 may be rectangular, as shown. Alternatively, it may be circular, oval, or of another shape. Bending points 13 are the points at which semicircular end sections 19 begin. Values for R may be, for example, between 1.2 and 1.4 mm, and values for t may be between 0.5 and 1.0 mm, for staples of length spans between 6 and 18 mm. Preferably, for staples of other sizes, similar relationships are maintained between L and R, L and t and R and t. In accordance with an alternative embodiment of the present invention, end sections 19 may be elliptical. Semicircular or elliptical end sections 19 have two advantages over clamping portions 16 (FIG. 2A):

1. since there is no 90° corner that is memorized, length span L of staple 10 may be adjusted in the martensitic phase, for example, by moving bending points 13 along semicircular end sections 19, so as to increase length span L; and
2. pointed edges 18 (FIG. 2B) are arranged to dig into the bone when staple 10 resumes its memorized shape.

In accordance with other embodiments of the present invention, staple 10 may be asymmetrical, having, for example, one leg 14 (FIG. 2A) that is shorter than the other, or one end section 19 (FIG. 2B) with a different radius of curvature R than the other. Additionally, staple 10 may have more than two legs, for example, three, four, or six legs. In accordance with still other embodiments of the present invention, one or more of legs 14 and clamping portions 16 (FIG. 2A) may coil around an axis defined by legs 14. Similarly staple 10 may have more than two semicircular end sections 19. For example, staple 10 may have 3, 4, 5, or 6 semicircular end sections 19, so as to resemble a crab. In accordance with the present invention, staple 10 may be manufactured by any known process for bone staples, and in particular, any known process for SMA bone staples.

Figure 3A:
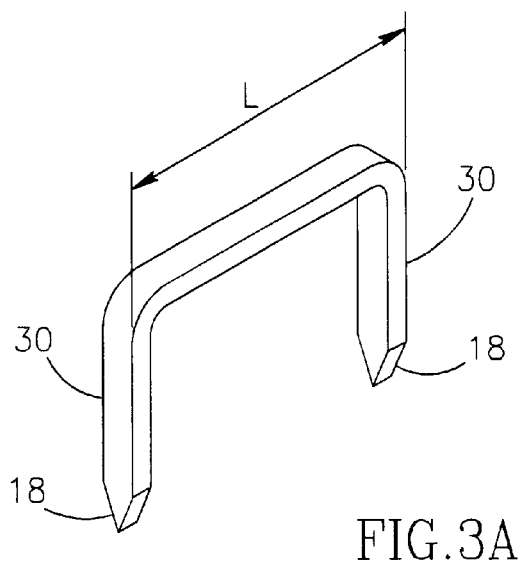
FIGS. 3A–3F schematically illustrate a method of using SMA staples for bone fixation, in accordance with the present invention.

Reference is now made to FIGS. 3A–3F, which together schematically illustrate a method of using at least one SMA staple 10 for bone fixation, in accordance with a preferred embodiment of the present invention. Preferably, the method includes the following steps:

1. As seen in FIG. 3A, clamping portions 16 (FIG. 2A) or end sections 19 (FIGS. 2B and 2C) are straightened, to form straightedges 30, in order to facilitate insertion into the bone. Preferably, the straightening plastic deformation is performed while staple 10 is fully martensitic. In accordance with a first embodiment of the present invention, which is the preferred embodiment, SMA staple 10 is fully austenitic at body temperature and is cooled to below room temperature, for example to 0–5° C., or lower, for the straightening deformation in the martensitic phase. In accordance with a second embodiment of the present invention, SMA staple 10 is fully martensitic at room temperature, and is straightened at room temperature.

Figure 3B:
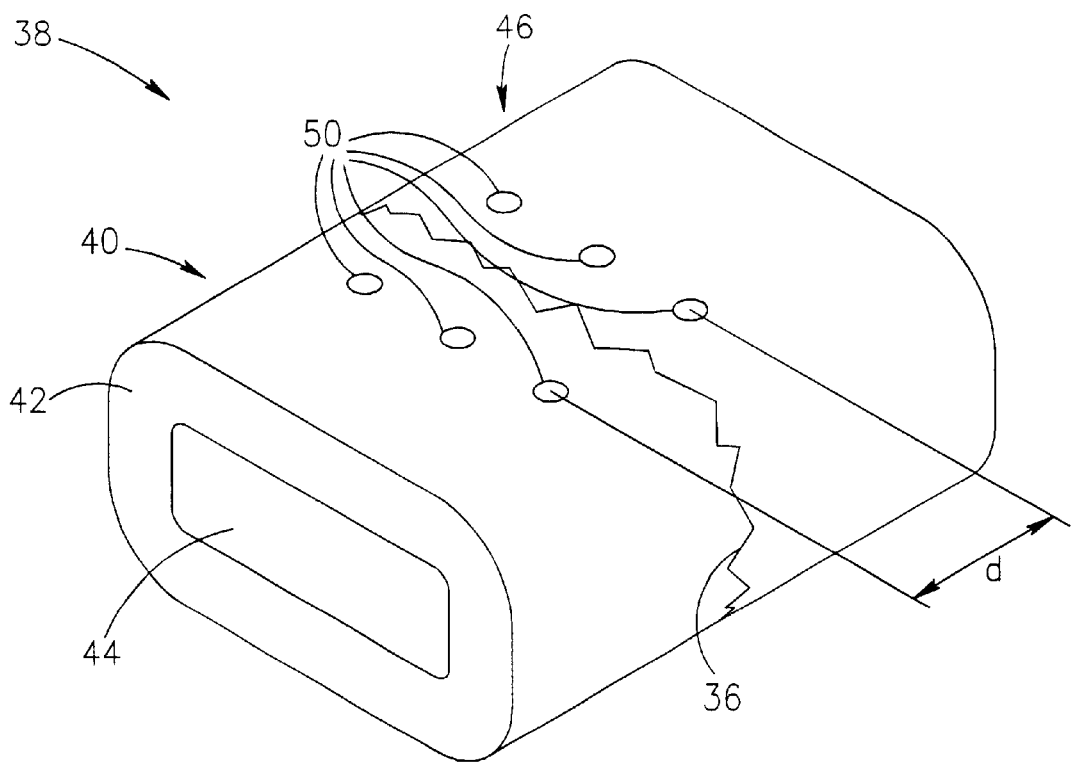

2. As seen in FIG. 3B, at least one pair of bores 50, and preferably, several pairs of bores 50 are drilled into a fractured bone 38, having a first fragment 40, a second fragment 46, and a fracture interface 36. Bone 38 has a hard, cortical exterior tissue 42, and a soft cancellous interior tissue 44. Each pair of bores 50 includes one bore in bone fragment 40, and another bore in bone fragment 46, across interface 36. A pair of bores 50 has a distance span d between the two bores that form the pair, wherein d depends on the nature of the fracture and the nature of interface 36. Preferably, a single value of d is used for all pairs of bores 50. However, d may have a different value for each pair of bores 50.

Figure 3C:
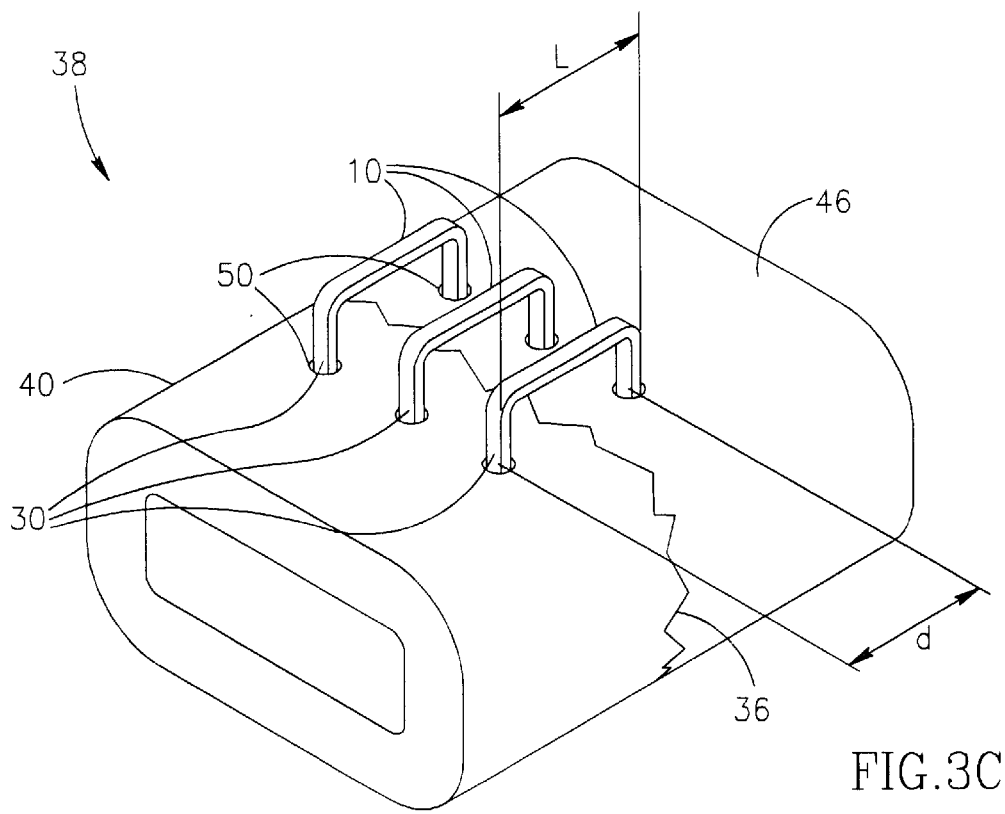

3. As seen in FIG. 3C, at least one staple 10 with straightedges 30, and preferably several staples 10 with straightedges 30, are inserted into bore pairs 50. Each staple 10 includes length span L which is substantially the same as distance span d between bores 50 that form a pair. In accordance with the prior art, staples 10 must be supplied with a wide range of length spans, to suit different bone fractures. However, in accordance with the present invention, a method for adjusting length span L of staple 10 is described hereinbelow, in conjunction with FIGS. 4A–11C. The method averts the need to provide staples in a wide range of dimensions and allows a manufacturer to provide staples of only two or three standard dimensions for each type of application, wherein the staples can be further adjusted before insertion into the bone.

Figure 3D:
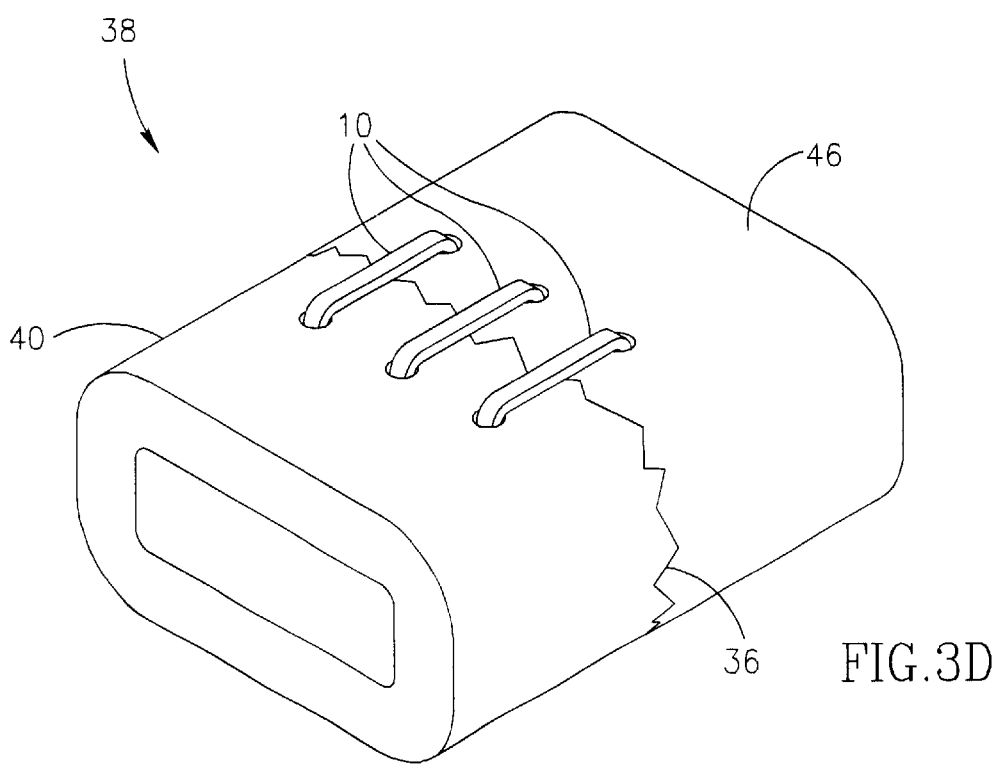

4. As seen in FIG. 3D, staples 10 are fully inserted into bone 38.

5. As seen in a cross-sectional view of bone 38, in FIG. 3E, staples 10 are inserted so that legs 14 penetrate cortical bone tissue 42 and straightedges 30 protrude from cortical bone tissue 42 into cancellous bone tissue 44.

Figure 1A:
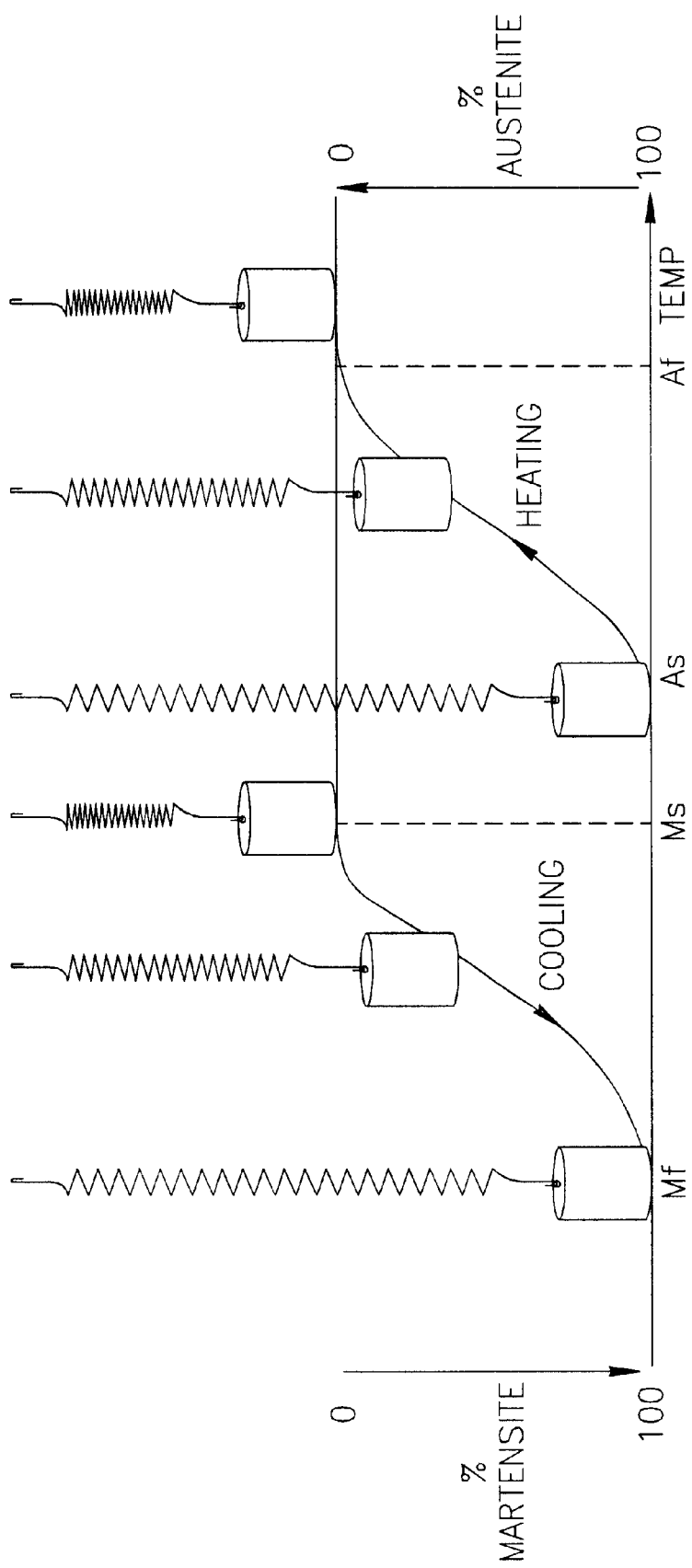
FIGS. 1A and 1B schematically illustrate a typical temperature hysteresis and typical elastic stresses, es, in phase transitions, for a shape-memory alloy, in accordance with the prior art.
Figure 1B:
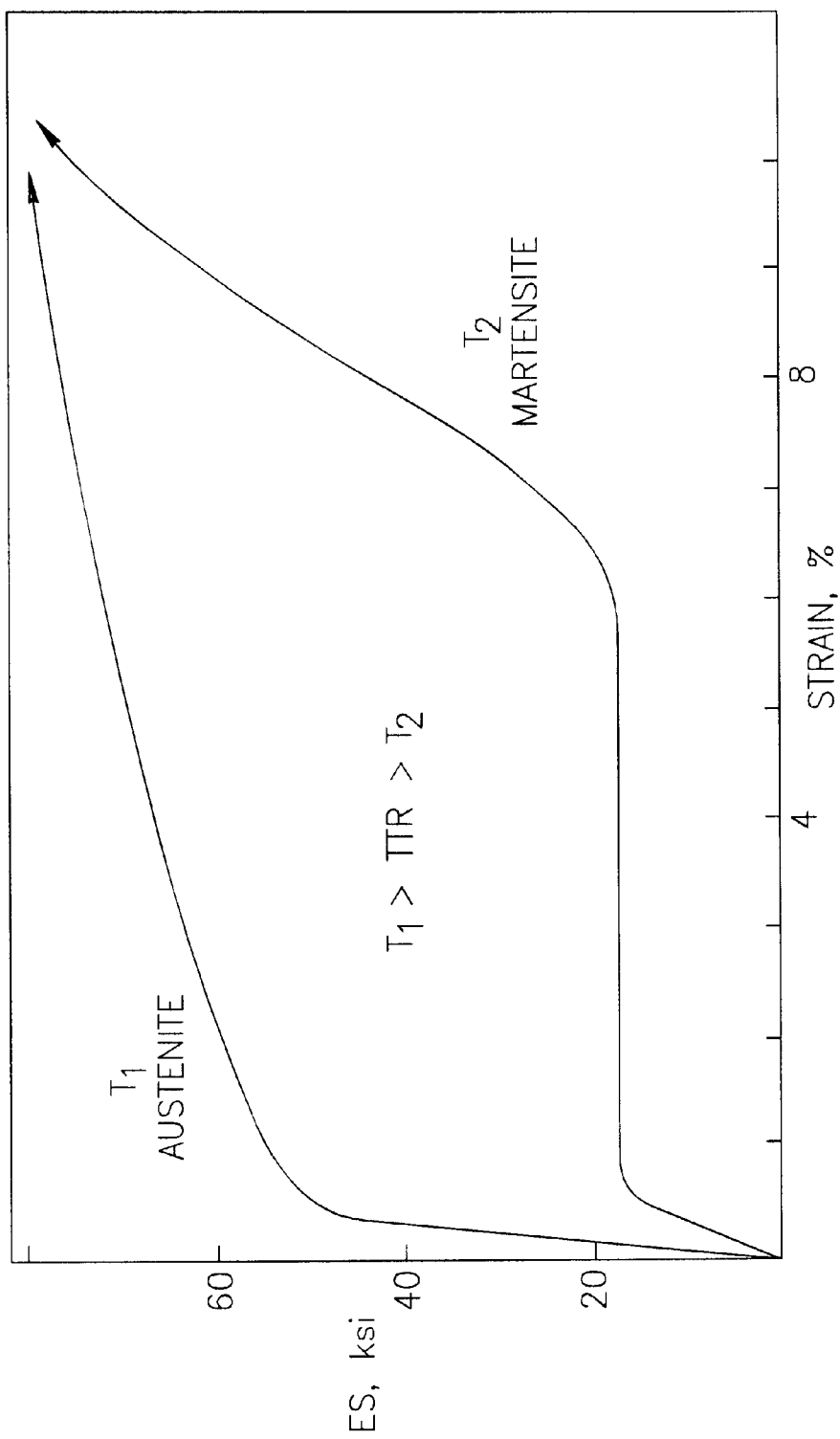
Figure 1D:
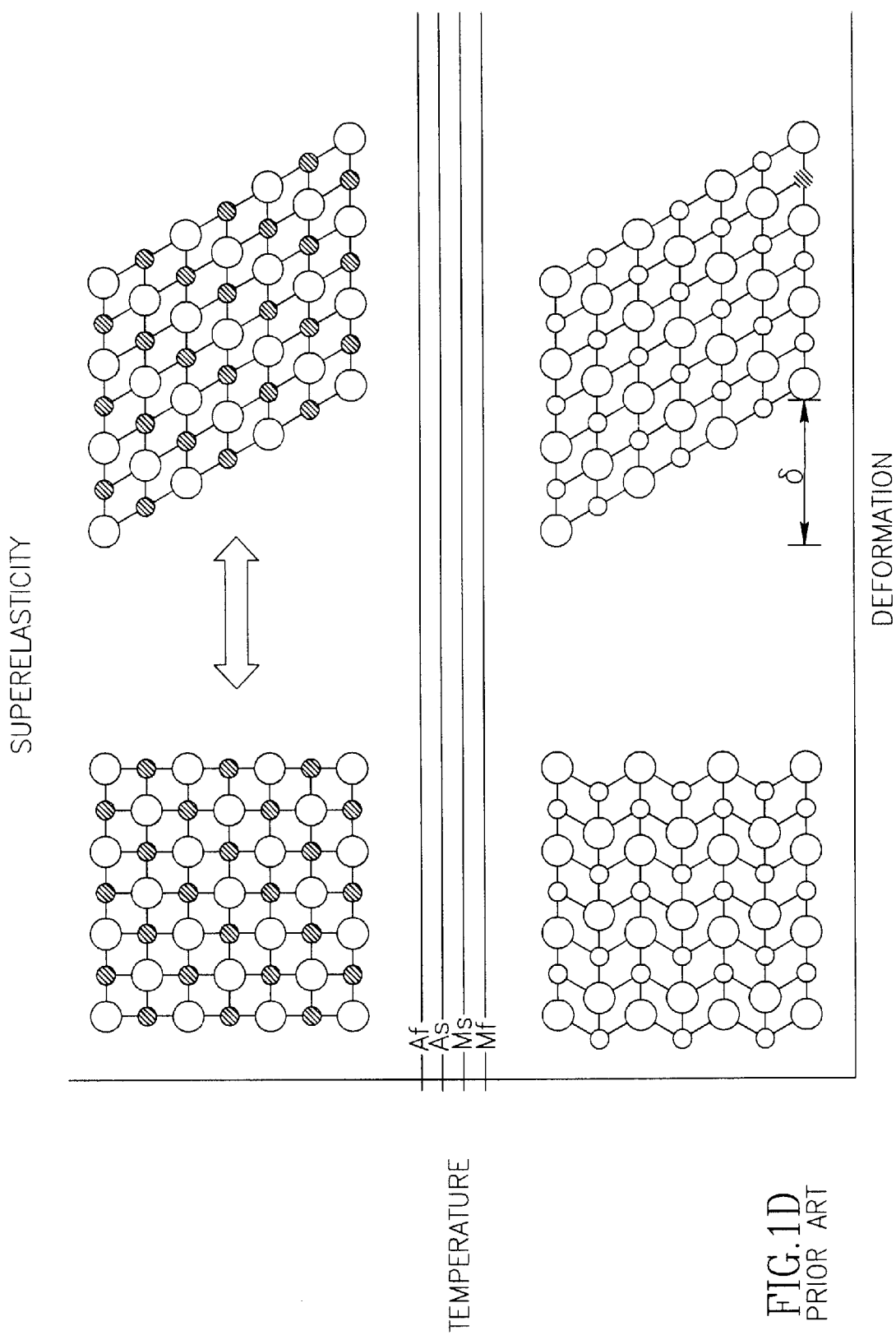
FIG. 1D schematically illustrates a typical cyclic transformation of a shape-memory alloy, between an austenitic phase and a stress-induced martensitic phase, in accordance with the prior art.
Figure 3E:
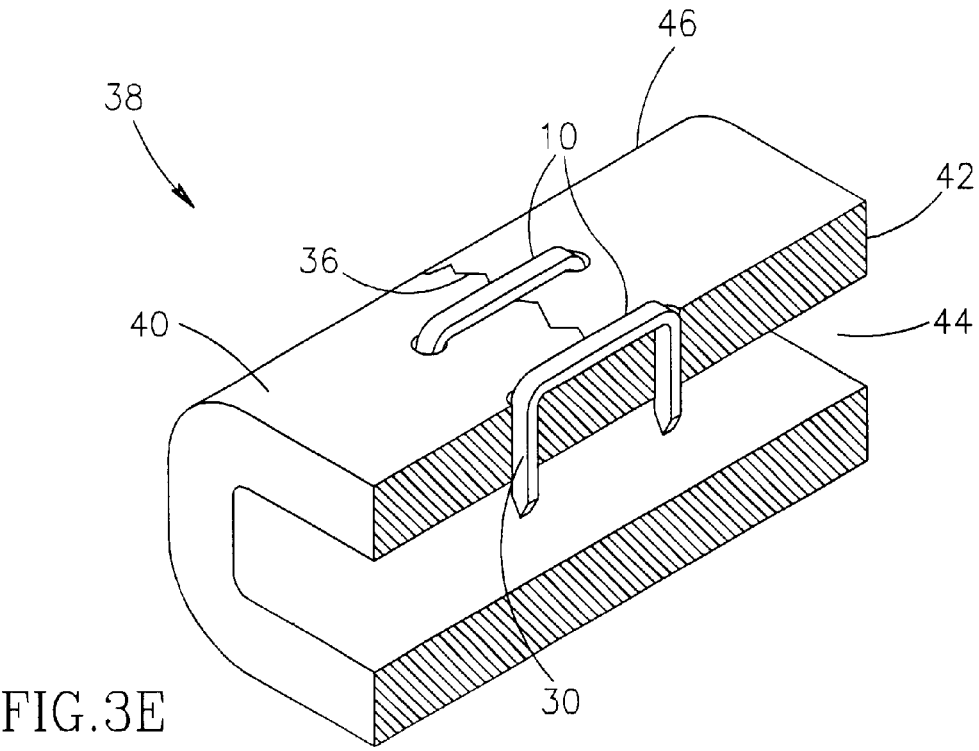
Figure 3F:
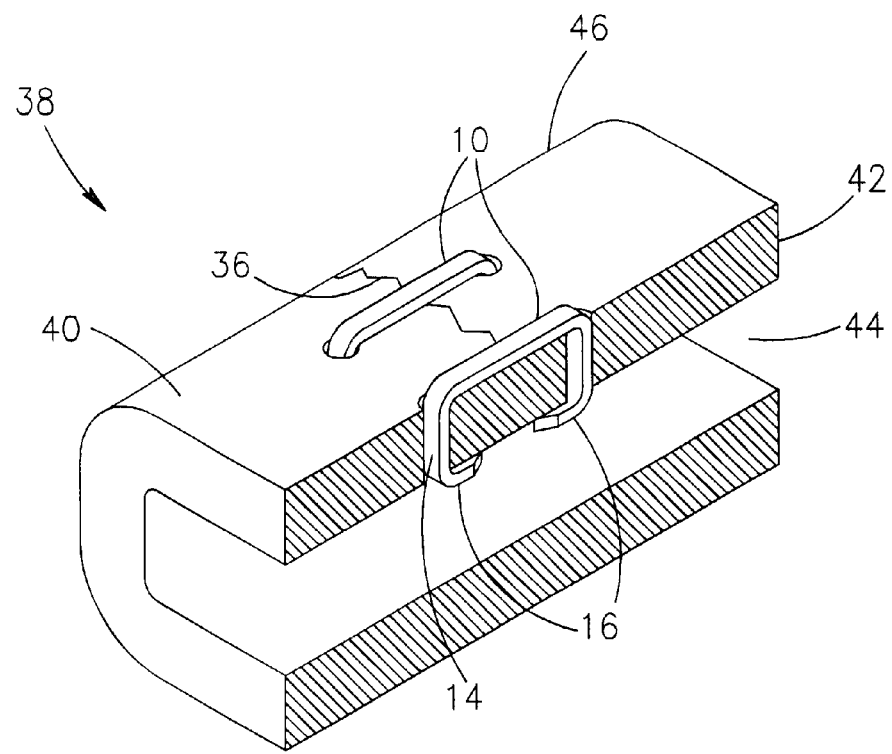

6. As seen in FIG. 3F, in accordance with the first embodiment of the present invention, in the body, staples 10 warm up to body temperature and become fully austenitic, resuming their memorized shape of FIG. 2A or 2B, and clamping bone fragments 40 and 46 together. Preferably, staples 10 have been imparted with super-elasticity, so as to provide dynamic osteosynthesis of the bone fragments. In accordance with the second embodiment of the present invention, staples 10 must be locally heated to a temperature above $A_f$ (FIG. 1A), which may be for example, 42–45° C., for transforming staples 10 to the fully austenitic phase. When fully austenitic, staples 10 resume their memorized shape and clamp bone fragments 40 and 46 together. The memorized shape is maintained in the body, even when body temperature is below $A_f$ (FIG. 1A).

Figure 4A:
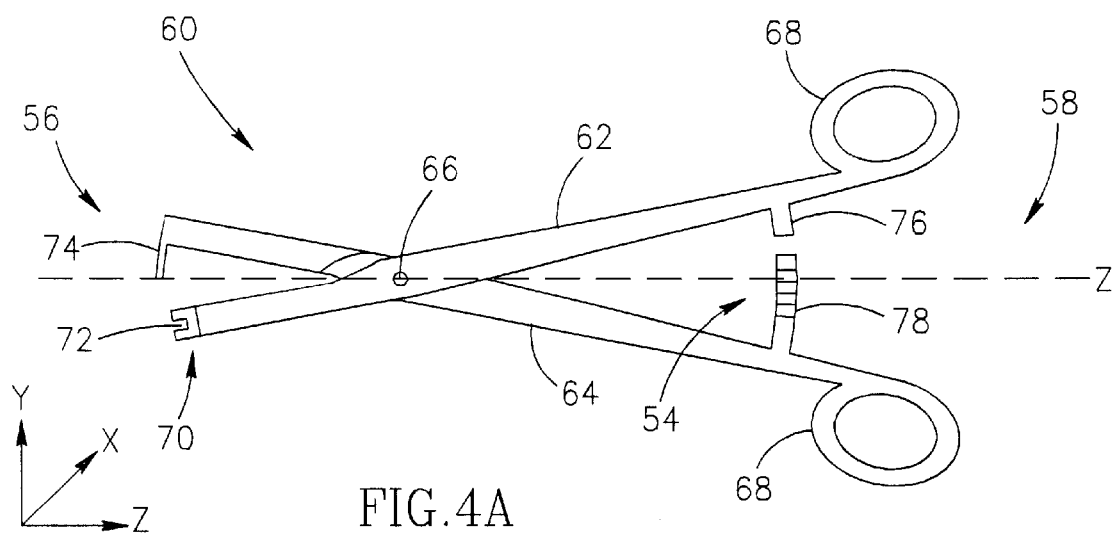
FIGS. 4A–4D schematically illustrate apparatus for increasing a length span of a staple, in accordance with a preferred embodiment of the present invention.

Reference is now made to FIGS. 4A–4D which together, schematically illustrate scissors-like apparatus 60 for increasing length span L (FIGS. 2A–2C) of staple 10, in accordance with a preferred embodiment of the present invention. As seen in FIG. 4A, apparatus 60 has a proximal end 58 and a distal end 56 with respect to a user (not shown). Apparatus 60 includes a first prong 62 and a second prong 64, joined by a swivel pin 66, at a point somewhere between proximal end 58 and distal end 56, arranged to slide past each other at distal end 56. Apparatus 60 further includes finger-gripping components 68, arranged on first and second prongs 62 and 64, at proximal end 58, for opening and closing apparatus 60, thus facilitating the sliding of first and second prongs past each other. Apparatus 60 defines a z-axis of an x;y;z coordinate system, parallel to its longitudinal axis.

Figure 4B:
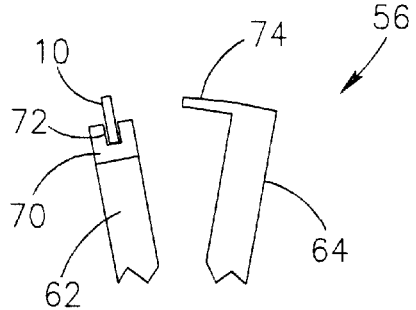
Figure 4C:
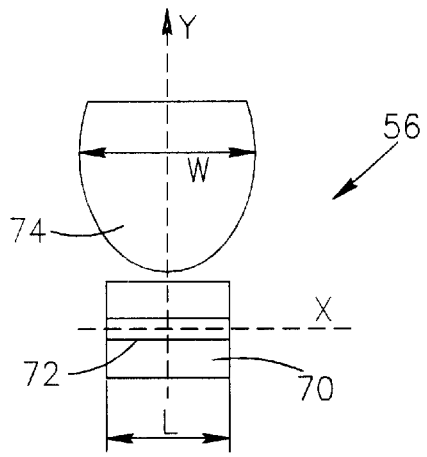

As seen in FIG. 4B, which illustrates a side view of distal portion 56 and in FIG. 4C, which illustrates an end view of distal portion 56, first prong 62 further includes a staple receptor 70, which has a channel 72, for mounting staple 10 thereon. Channel 72 defines an x-axis of the x;y;z coordinate system, parallel to length span L of staple 10 and perpendicular to the direction of opening and closing of apparatus 60.

Additionally, second prong 64 further includes a thin, cam-like head 74, having a width span w that increases in the direction of increasing y. Thin, cam-like head 74 is operable to increase length span L of staple 10.

Preferably, as finger-gripping components 68 are moved towards each other, for closing apparatus 60, thin, cam-like head 74 is arranged to slide between staple receptor 70 and staple 10 mounted thereon, in the direction of increasing y, for a predetermined y value, thus wedging itself between staple receptor 70 and staple 10, deforming staple 10 to width w of thin, cam-like head 74 at the predetermined y value.

Figure 4D:
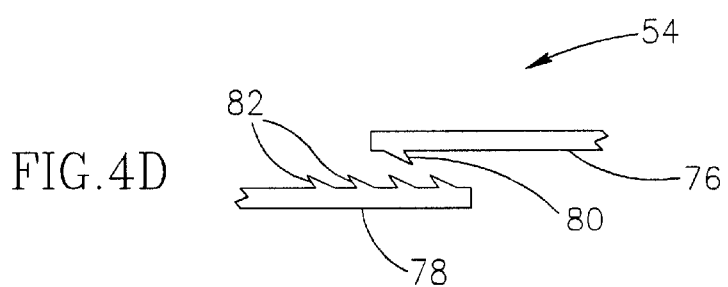

Additionally, as seen in FIG. 4D, apparatus 60 includes a mechanical stopping component 54, for controlling the amount of closure between first and second prongs 62 and 64, thus predetermining the value of y, and controlling the amount of length-span increase to staple 10. Preferably, mechanical stopping component 54 includes a first rod 76 with a hook 80, arranged on one of the prongs, and a second rod 78 with a plurality of notches 82, arranged on the other prong, generally near proximal end 58. Each of plurality of notches 82 is arranged to lock with hook 80. The distance between notches 82 is calculated to yield length-span increases of desired increments, for example, 1 mm or 0.5 mm. By closing apparatus 60 only to a specific notch 82, a desired length-span increase of staple 10 mounted in channel 72 is achieved.

Figure 5A:
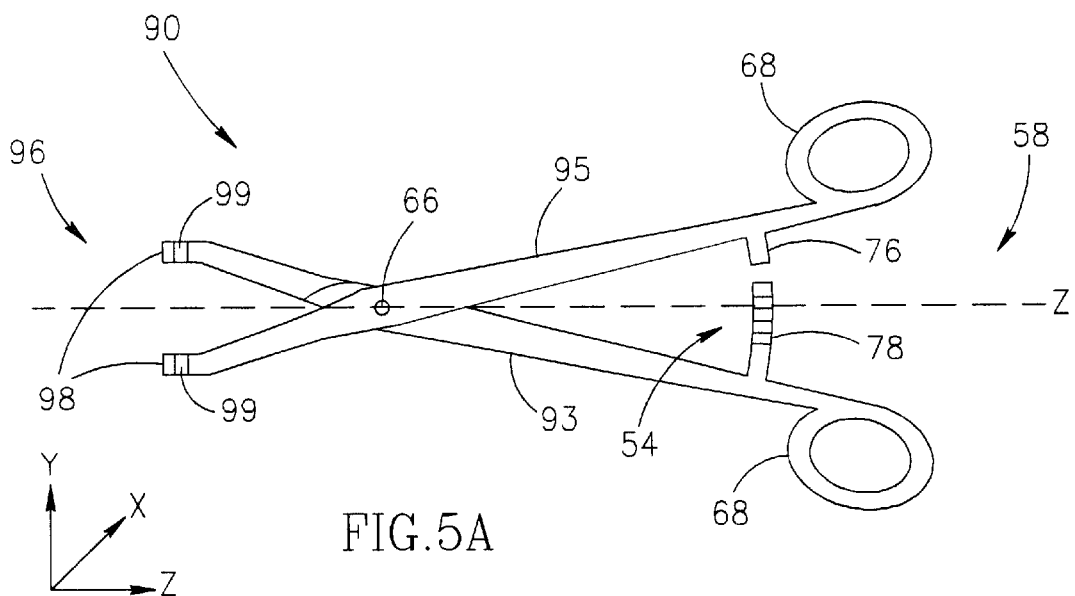
FIGS. 5A and 5B schematically illustrate apparatus for increasing a length span of a staple, in accordance with a first alternative embodiment of the present invention.
Figure 5B:
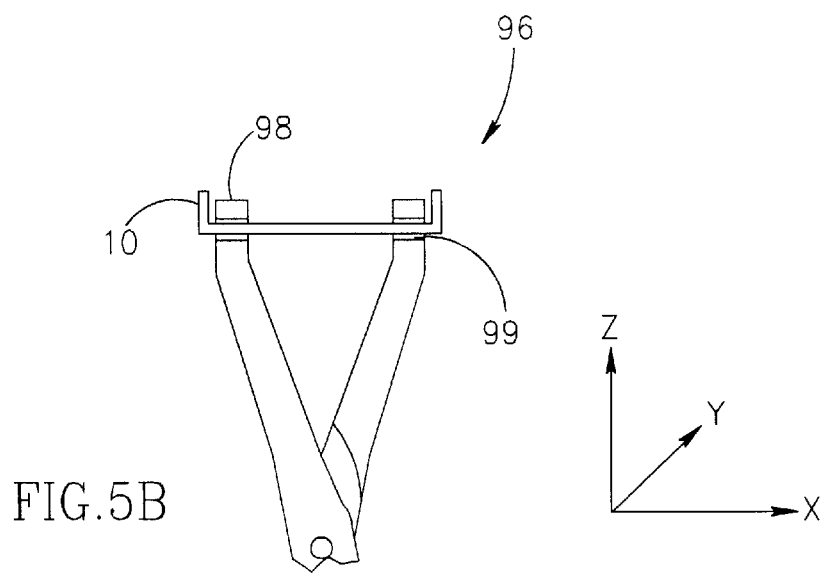

Reference is now made to FIGS. 5A and 5B, which together, schematically illustrate scissors-like apparatus 90 for increasing length span L (FIGS. 2A–2C) of staple 10, in accordance with a first alternative embodiment of the present invention. As seen in FIG. 5A, apparatus 90 has proximal end 58 and a distal end 96 with respect to the user. Apparatus 90 includes a first prong 95 and a second prong 93, joined by a swivel pin 66, at a point somewhere between proximal end 58 and distal end 96, arranged for closing and opening at distal end 96. Apparatus 90 defines a z-axis of an x;y;z coordinate system, parallel to its longitudinal axis.

In accordance with the present embodiment, first and second prongs 95 and 93 include, at distal end 96, tips 98, which include slits 99, arranged for receiving staple 10 thereon, when apparatus 90 is closed. Tips 98 define an x-axis of the x;y;z coordinate system between them. Tips 98 and slits 99 may be arranged for receiving staple 10 so that its web 12 is parallel with the x-axis and its legs 14 are parallel with the z-axis. Alternatively, tips 98 and slits 99 may be arranged for receiving staple 10 so that its web 12 is parallel with the x-axis and its legs 14 are parallel with a y-axis.

Preferably, as seen in FIG. 5B, staple 10 is positioned in slits 99 when apparatus 90 is closed. By opening apparatus 90, tips 98 pry staple 10 wider, increasing its length span.

Preferably, apparatus 90 further includes, at proximal end 58, mechanical stopping component 54, for controlling the amount of opening between first prong 95 and second prong 93, thus predetermining the extent of prying staple 10, and the incremental length-span increase to staple 10.

Figure 6A:
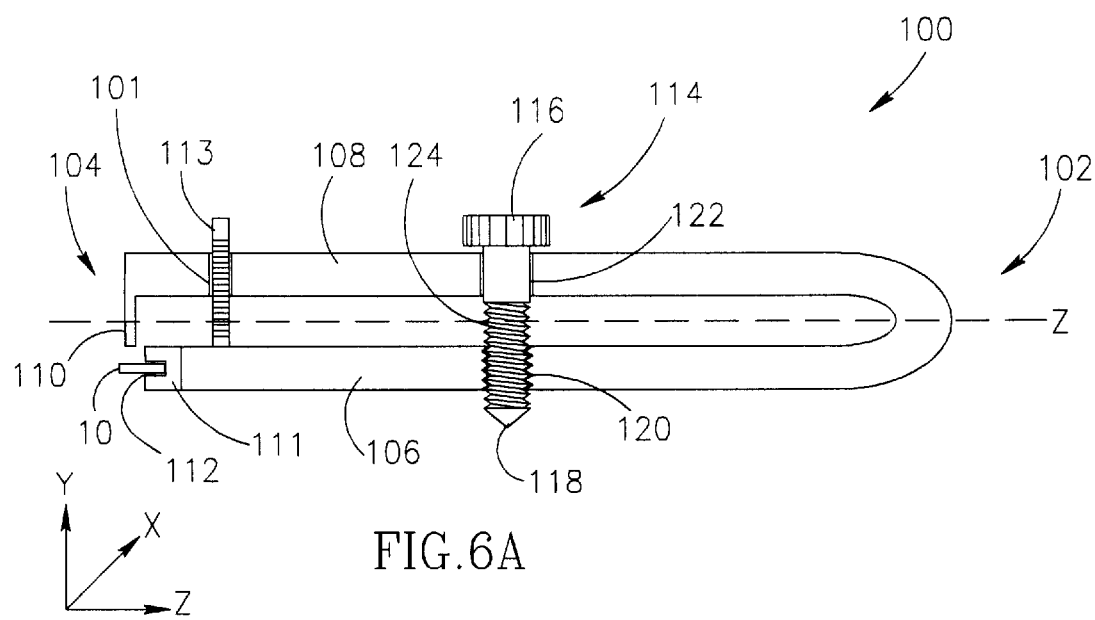
FIGS. 6A–6C schematically illustrate apparatus for increasing a length span of a staple, in accordance with a second alternative embodiment of the present invention.
Figure 6B:
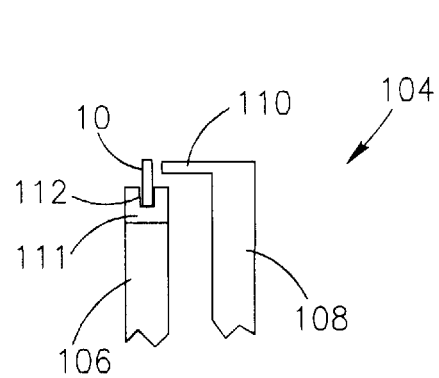
Figure 6C:
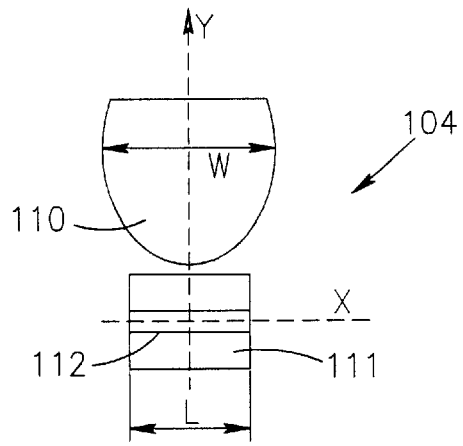

Reference is now made to FIGS. 6A–6C, which together, schematically illustrate apparatus 100 for increasing length span L (FIGS. 2A–2C) of staple 10, in accordance with a second alternative embodiment of the present invention. As seen in FIG. 6A, apparatus 100 has a proximal end 102 and a distal end 104 with respect to the user. Apparatus 100 includes a first prong 106 and a second prong 108, joined by a bolt 114, at a point somewhere between proximal end 102 and distal end 104, arranged for selectably increasing and decreasing the distance between first prong 106 and second prong 108. Apparatus 100 defines a z-axis of an x;y;z coordinate system, parallel to its longitudinal axis.

As seen in FIG. 6B, which illustrates a side view of distal portion 104 and in FIG. 6C, which illustrates an end view of distal portion 104, first prong 106 further includes a staple receptor 111, which has a channel 112, for mounting staple 10 thereon. Channel 112 defines an x-axis of the x;y;z coordinate system, parallel to length span L of staple 10 and perpendicular to the direction of increasing and decreasing distances between first prong 106 and second prong 108.

Additionally, second prong 108 further includes a thin, cam-like head 110, having a width span w that increases in the direction of increasing y. Thin, cam-like head 110 is operable to increase length span L of staple 10.

Furthermore, second prong 108 includes a through hole 122 and first prong 106 includes a threaded, preferably through hole 120. Bolt 114 includes a head 116, a tip 118, and a threaded portion 124. Preferably, head 116 is a relatively large knob 116, arranged to be rotated by fingers of the user. Preferably, bolt 114 is arranged inside through hole 122 and internally thread hole 120.

Thus, as knob 116 is rotated in the direction of threading portion 124 further into threaded hole 120, the distance between first prong 106 and second prong 108 is decreased, and cam-like head 110 is wedged between channel 112 and a staple 10 mounted thereon, deforming staple 10 to width w of thin, cam-like head 110. The amount of deformation is determined by the number of turns of knob 116. Preferably, a gauge 113, which preferably protrudes from first prong 106 and is arranged to slide in a slit 101 in second prong 108, or arranged to slide along second prong 108, helps the user determine the distance between first and second prongs 106 and 108, and the amount of length increase that is applied to staple 10. Alternatively, a hand-held gauge, not physically attached to the prongs, may be used.

Figure 7:
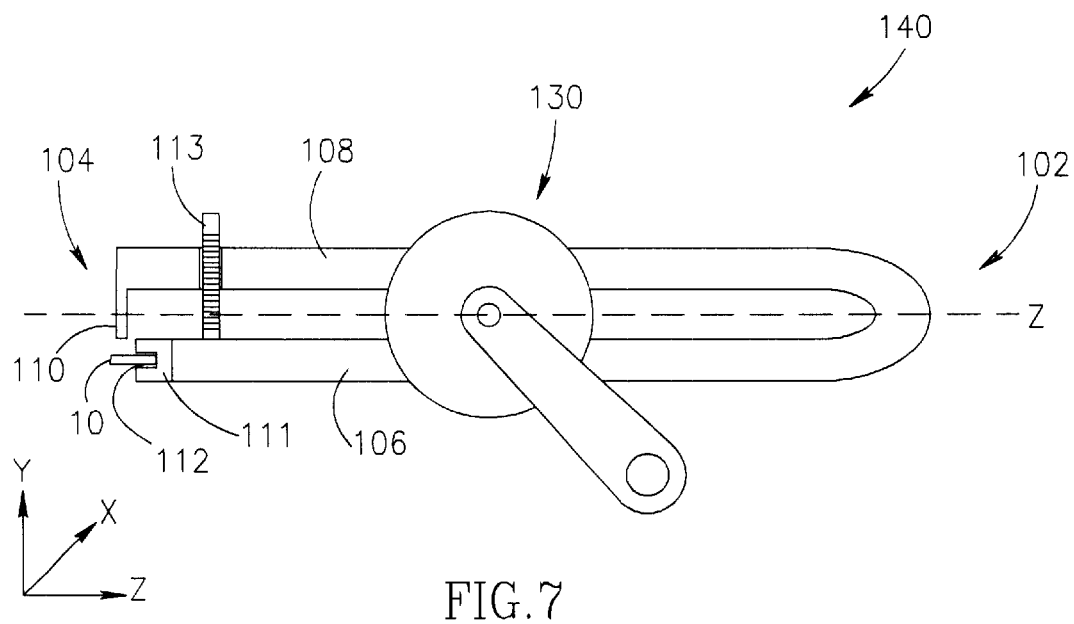
FIG. 7 schematically illustrates apparatus for increasing a length span of a staple, in accordance with a third alternative embodiment of the present invention.

Reference is now made to FIG. 7, which schematically illustrates apparatus 140 for increasing length span L of staple 10, in accordance with a third alternative embodiment of the present invention. In accordance with the present embodiment, prongs 106 and 108 are manipulated by a rotating knob 130, to selectably increase and decrease the distance between them.

In accordance with the present invention, the method of using any of apparatus 60 (FIG. 4A), apparatus 90 (FIG. 5A), apparatus 100 (FIG. 6A), or apparatus 140 (FIG. 7) is as follows:

1. As seen in FIG. 3A, staple 10, preferably of standard dimensions, having standard web length span L, and straightedges 30 is provided;
2. As seen in FIG. 3B, bore pairs 50 are drilled into fractured bone 38, across fracture interface 36, wherein each bore pair 50 is associated with distance d between the bores of the pair, and wherein d is equal to or greater than length span L of staple 10;
3. Where d>L, the surgeon (not shown) will adjust the length span L of staple 10 by increasing it, using any of the aforementioned apparatus; and
4. As seen in FIGS. 3C–3E, staple 10 of adjusted length span L, so that L is equal to d, is inserted into bone 38.

In accordance with a preferred embodiment of the present invention, staple 10 may be employed in a plastically deformed state that results from the length-span increase. In other words, the deformed shape that results from the length-span increase is the final shape, and staple 10 may be used to provide bone fixation, while in a stress-induced martensite state.

In accordance with a preferred embodiment of the present invention, staples 10 of length spans between 6 and 18 are provided in three length spans, of 4 mm increments, as follows:

1. A staple of 6 mm length span L, arranged for length spans between 6 and 10 mm.
2. A staple of 10 mm length span L, arranged for length spans between 10 and 14 mm.
3. A staple of 14 mm length span L, arranged for length spans between 14 and 18 mm.

Alternatively, staples 10 of length-spans between 5 and 30 are provided in five length spans, of 5 mm increments, as follows:ps 1. A staple of 5 mm length span L, arranged for length spans between 5 and 10 mm.
2. A staple of 10 mm length span L, arranged for length spans between 10 and 15 mm.
3. A staple of 15 mm length span L, arranged for length spans between 15 and 20 mm.
4. A staple of 20 mm length span L, arranged for length spans between 20 and 25 mm.
5. A staple of 25 mm length span L, arranged for length spans between 25 and 30 mm.

Alternatively, staples 10 of length spans between 10 and 100 mm are provided in ten length spans, of 10 mm increments, or in 20 length spans of 5 mm increments.

Alternatively, other length spans and other incremental increases are provided.

Figure 8:
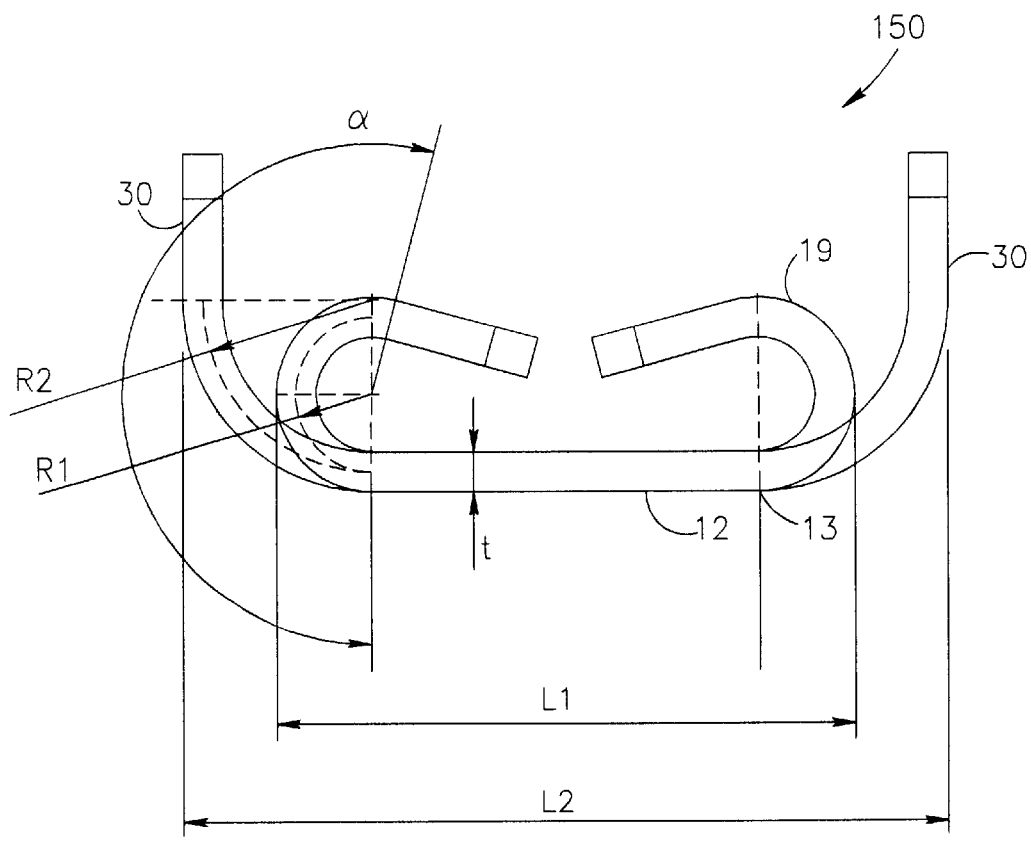
FIG. 8 schematically illustrates a staple for bone fixation, in accordance with a preferred embodiment of the present invention.

Reference is now made to FIG. 8, which schematically illustrates a staple 150, in accordance with a preferred embodiment of the present invention. In its austenitic shape, staple 150 is similar to staple 10 of FIGS. 2B and 2C. Staple 150 includes web 12 of a length L1, thickness t and two semicircular end sections 19 of a radius R1, measured as the inner radius plus half thickness t. Bending points 13 are the points at which semicircular end sections 19 begin. Values for R1 may be, for example, between 1.2 and 1.4 mm, and values for t may be, for example, between 0.5 and 1.0 mm, for staples of length spans L1 between 6 and 18 mm.

In accordance with the preferred embodiment of the present invention, staple 150 is plastically deformed to simultaneously achieve the following:

1. form straightedges 30, to facilitate insertion into the bone; and
2. increase length span L1 to a length span L2.

This type of plastic deformation can be achieved, for example, by apparatus 90 (FIGS. 5A and 5B).

Preferably, each semicircular end section 19 has an angle α associated therewith, measured from point 13, wherein α is generally greater than 90°. Preferably, staple 150 is plastically deformed so that α becomes 90°. When this happens, a new radius of curvature, R2, is generated, and the length span of web 12 increases from L1 to L2.

Preferably, the plastic deformation is performed while staple 150 is fully martensitic. In accordance with a preferred embodiment of the present invention, staple 150 is fully austenitic at body temperature and is cooled to below room temperature, for example to 0–5° C., or lower, for the plastic deformation in the martensitic phase. Alternatively, staple 150 is fully martensitic at room temperature, and is plastically deformed at room temperature. Alternatively, staple 150 posses superelasticity and the plastic deformation is performed while staple 150 is fully austenitic, to form stress-induced martensite.

In accordance with a preferred embodiment of the present invention, staple 150 may be employed in its plastically deformed state, which resulted from the length-span increase. In other words, staple 150 may be employed to provide bone fixation, while it is in a stress-induced martensite state.

In accordance with the preferred embodiment of the present invention, the plastic deformation is maintained within an allowable range for restoration of the austenitic shape, as described hereinbelow.

Reference is now made to FIGS. 9A–9C, which illustrate, in a table format, plastic deformation strains, δ, for different ratios R1/t and different initial angle α and a final angle of 90°, for the staple of FIG. 8. Generally, complete restoration of the austenitic shape occurs when the plastic deformation strain does not exceed 10.4%. Yet, partial restoration of the austenitic shape occurs when the plastic deformation strain does not exceed 15%, which may be considered the allowable limit for plastic deformation.

For example, given an R1 value of 1.4 mm and a t value of 0.7 mm, so that R1/t=2.00, and given an initial angle α of 165°, the plastic deformation strain, associated with changing the angle α to 90°, as read from FIGS. 9A–9C, is 10%, well below the allowable limit of 15%.

The darkly shaded portion of FIGS. 9A–9C illustrates the allowable operational range for plastic deformation of staple 150. The lightly shaded portion of FIGS. 9A–9C illustrates the desired operational range of plastic deformation of staple 150. A special shading is used for values near 2.00, which are generally preferred.

It will be appreciated by persons versed in the art, that a similar analysis may be made for a staple of another geometry.

Figure 10A:
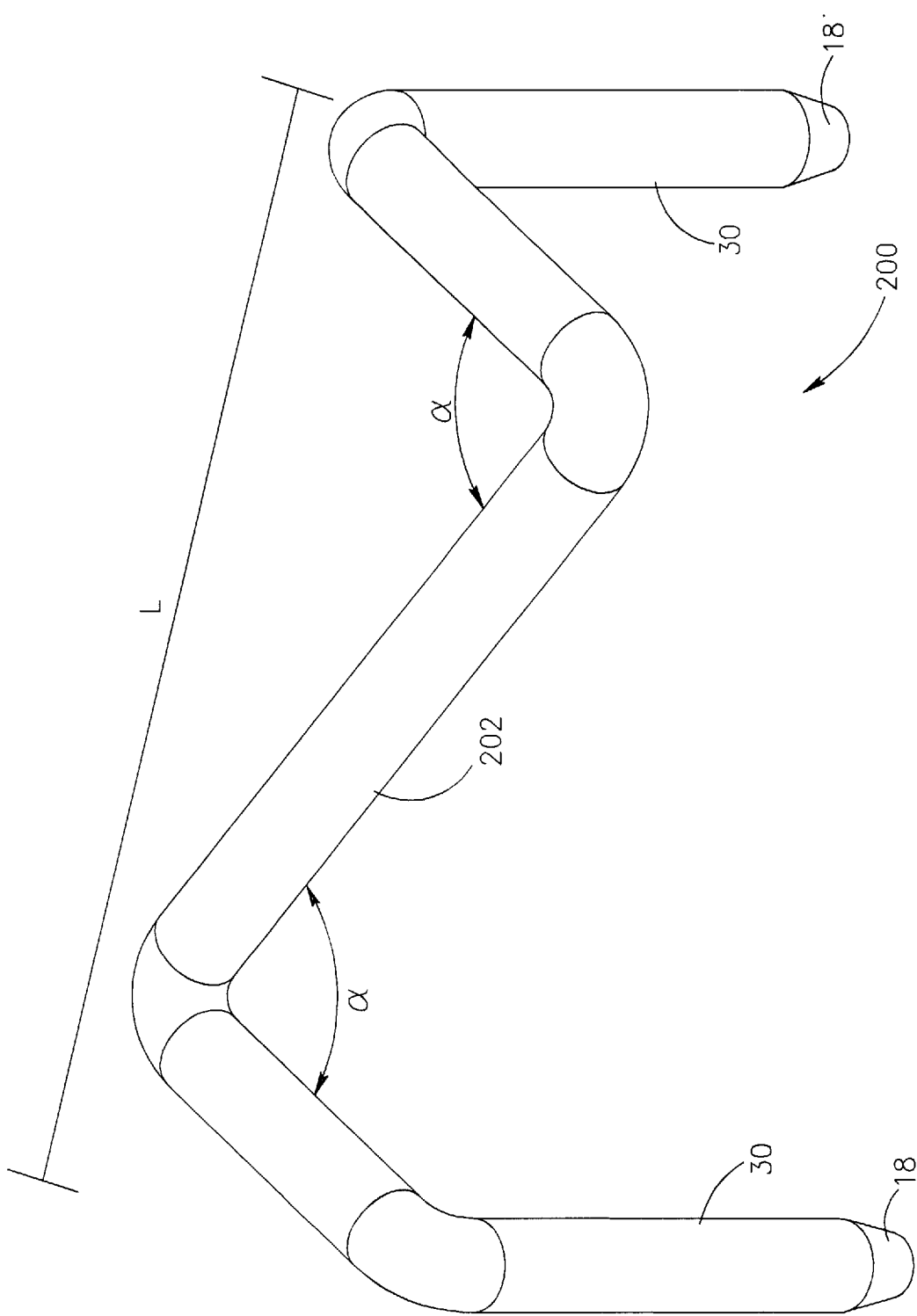
FIGS. 10A and 10B schematically illustrate a staple for bone fixation, in accordance with an alternative embodiment of the present invention.
Figure 10B:
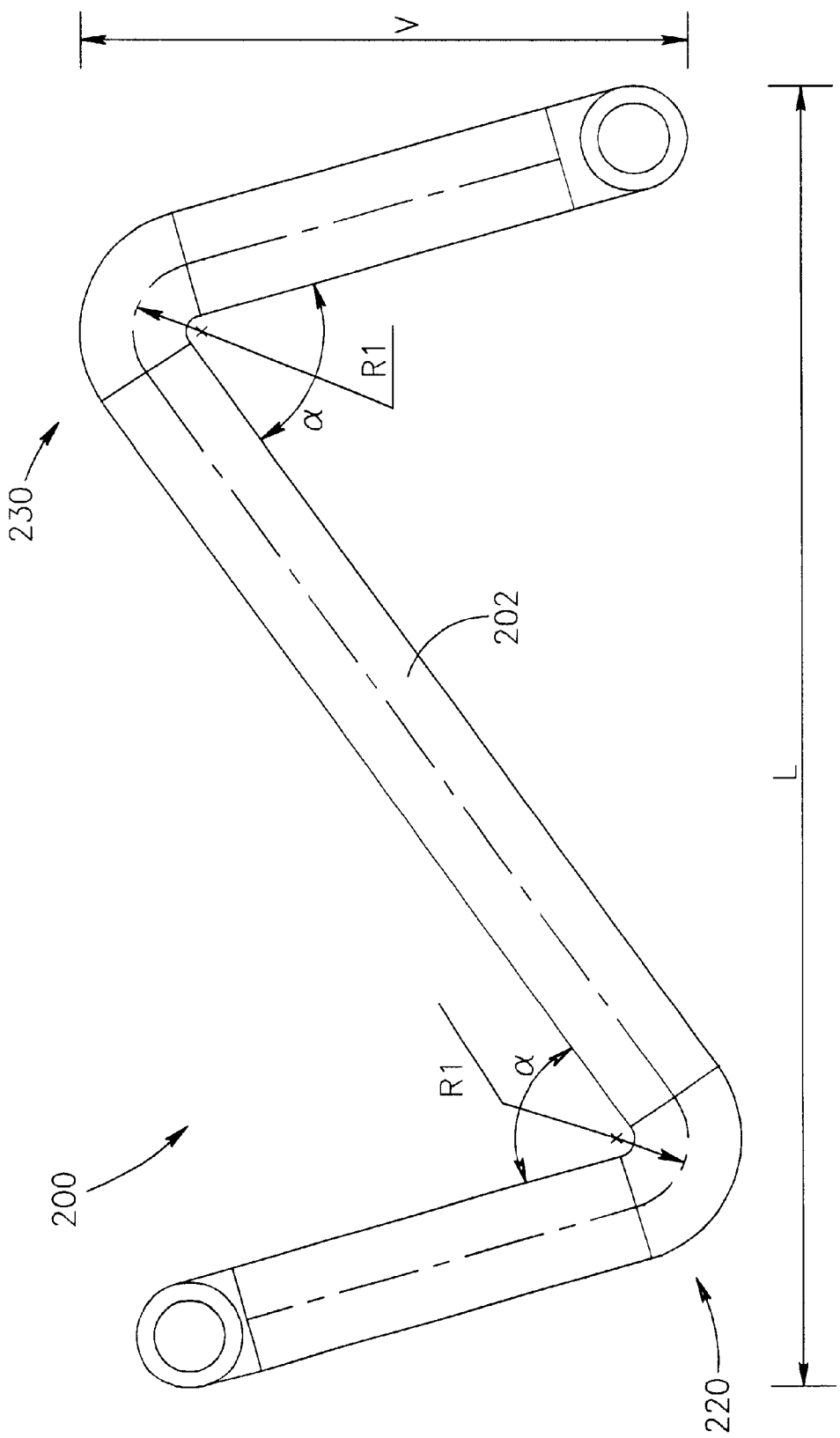

Reference is now made to FIGS. 10A and 10B, which schematically illustrate a staple 200, in accordance with an alternative embodiment of the present invention. Staple 200 is shown with straightedges 30, in a manner similar to staple 10 of FIG. 3A. In its austenitic shape, staple 200 includes a web 202, which has a length span L, at least one curvature 220, having a radius R1 and an angle α, and an effective web width V. Additionally, staple 200 may have an additional curvature 230, also having radius R1 and angle α. However, curvature 220 may have different values of R1 and α from those of curvature 230. Preferably, length span L of staple 200 may be increased by straightening, or partially straightening at least one curvature 220, or curvatures 220 and 230. Preferably, staple 200 is formed of a shape-memory alloy, and preferably, straightening includes straightening by plastically deforming web 202, while maintaining the values of R1 and α, so that the plastic deformation does not exceed 15%, as seen in FIGS. 9A–9C.

Preferably, the plastic deformation is performed while staple 200 is fully martensitic. In accordance with a preferred embodiment of the present invention, staple 200 is fully austenitic at body temperature and is cooled to below room temperature, for example to 0–5° C., or lower, for the plastic deformation in the martensitic phase. Alternatively, staple 200 is fully martensitic at room temperature, and is plastically deformed at room temperature. Alternatively, staple 200 posses superelasticity and the plastic deformation is performed while staple 200 is fully austenitic, to form stress-induced martensite.

In accordance with a preferred embodiment of the present invention, staple 200 may be employed in its plastically deformed state, which resulted from the length-span increase. In other words, staple 200 may be employed to provide bone fixation, while it is in a stress-induced martensite state.

Figure 11A:
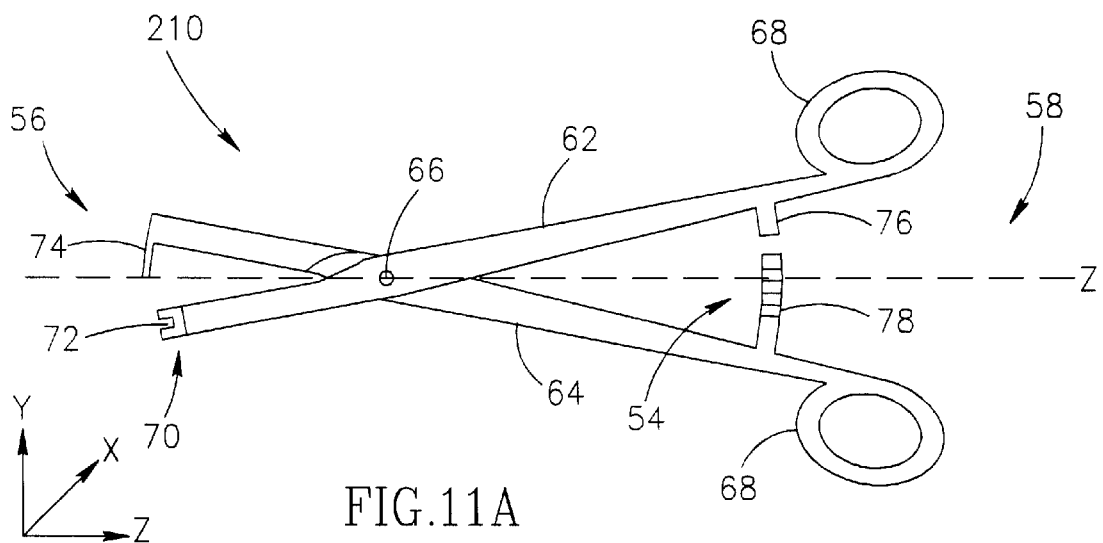
FIGS. 11A–11C schematically illustrate apparatus for increasing a length span of the staple of FIGS. 10A and 10B, in accordance with the present invention.
Figure 11B:
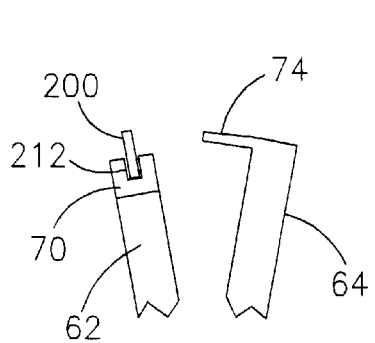
Figure 11C:
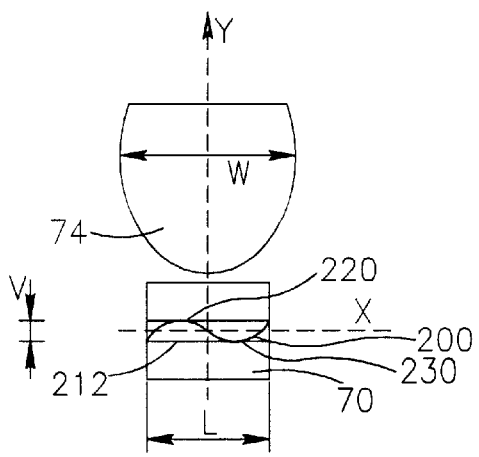

Reference is now made to FIGS. 11A–11C, which schematically illustrate apparatus 210 for increasing length span L of web 202 of staple 200. In essence, apparatus 210 is similar in construction and operation to apparatus 60 of FIGS. 4A–4D. However, apparatus 210 has a channel 212 of effective width V, arranged to receive staple 200 of effective web width V.

In accordance with a preferred embodiment of the present invention, staples 10, 150 and 200 are formed of a shape-memory alloy having a fully martensitic phase within a first temperature range, and having a fully austenitic phase within a second temperature range, which is higher than the first temperature range. Preferably, plastically deforming the staple includes plastically deforming the staple by reversible martensitic deformation.

Preferably, plastically deforming the staple by reversible martensitic deformation includes plastically deforming the staple at a temperature range of the fully martensitic phase.

Alternatively, plastically deforming the staple by reversible martensitic deformation includes plastically deforming the staple in a stress-induced martensitic phase at a temperature range of the fully austenitic phase.

It will be appreciated by persons skilled in the art, that the scope of the present invention is not limited by what has been specifically shown and described hereinabove, merely by way of example. Rather, the scope of the invention is limited solely by the claims, which follow.

What is claimed is:

1. Apparatus for increasing a length span of a staple, which includes:
   proximal and distal ends with respect to a user, which define a z-axis of an x;y;z coordinate system between them; and
   first and second prongs, joined by a system which provides a mechanical advantage to selectably bringing said first and second prongs together and pushing them apart,
   wherein said first prong further includes, at said distal end, a staple receptor, with a channel, for mounting said staple thereon, said channel defining an x-axis of the x;y;z coordinate system, parallel to said staple length span, and perpendicular to the direction of bringing first and second prongs together and pushing them apart, wherein said second prong further includes, at said distal end, a thin, cam-like head, having a width span that increases in the direction of increasing y, operable to increase said staple length span, and wherein, as said first and second prongs are brought together, said thin, cam-like head is arranged to slide between said staple receptor and said staple, mounted thereon, so as to wedge between said staple receptor and said staple and increase the length span of said staple.

2. Apparatus according to claim 1 and further including a mechanical stopping component, for controlling the amount by which said first and second prongs are brought together, hence, the length-span increase to said staple.

3. Apparatus according to claim 1 and further including a gauge, for measuring the amount by which said first and second prongs are brought together, hence, the length-span increase to said staple.

4. Apparatus according to claim 1, wherein said system which provides a mechanical advantage to selectably bringing said first and second prongs together and pushing them apart is a swivel pin.

5. Apparatus according to claim 1, wherein said system which provides a mechanical advantage to selectably bringing said first and second prongs together and pushing them apart is a threaded bolt.

6. Apparatus according to claim 1, wherein said system which provides a mechanical advantage to selectably bringing said first and second prongs together and pushing them apart is a pulley.

7. A method of increasing a length span of a staple, which includes the steps of:

employing prongs which define a z-axis of an x;y;z coordinate system, generally parallel with their longitudinal axis;

mounting the staple on a staple receptor, which is arranged on the first prong, and which defines an x-axis of the x;y;z coordinate system, parallel with a length direction of the staple; and sliding a thin cam, arranged on a second prong, and having a width which increases in the direction of increasing y, between the staple receptor and the staple mounted thereon, thus wedging the thin cam between the staple receptor and the staple; and plastically deforming the staple, to increase its length span.

8. A method according to claim 7, wherein said step of sliding a thin cam further includes sliding by a predetermined amount, thus predetermining the length-span increase of the staple.

9. A method according to claim 7, wherein the staple is formed of a shape-memory alloy having a fully martensitic phase within a first temperature range, and having a fully austenitic phase within a second temperature range, which is higher than the first temperature range, and wherein said step of plastically deforming the staple includes plastically deforming the staple by reversible martensitic deformation.

10. A method according to claim 9, wherein said step of plastically deforming the staple by reversible martensitic deformation includes plastically deforming the staple at a temperature range of the fully martensitic phase.

11. A method according to claim 9, wherein said step of plastically deforming the staple by reversible martensitic deformation includes plastically deforming the staple in a stress-induced martensitic phase at a temperature range of the fully austenitic phase.

12. A method of bone fixation with an SMA staple, which includes the steps of:

drilling at least one pair of bores across a fracture interface of a bone;

measuring the distance span between the two bores of the bore pair;

selecting an SMA staple having a length span which is smaller than the distance span;

plastically deforming the staple, to increase its length span, in accordance with the method of claim 7;

inserting the staple into the bores; and employing the staple in the plastically deformed state, which resulted from the length-span increase.

13. A staple for bone fixation, formed of a shape-memory alloy having a fully martensitic phase within a first temperature range, and having a fully austenitic phase within a second temperature range, which is higher than the first temperature range, which includes:

a web having a first length span and a thickness;

two bending points, forming the end points of said web; and two semicircular end sections, beginning from said bending points, having a radius of curvature (R1), an angle of curvature ($\alpha$) that is greater than 90°, and a thickness (t) which is substantially the same as said web thickness, wherein by plastically deforming said staple, reversibly, in the fully martensitic phase, to decrease said angle of curvature ($\alpha$) to 90°, said semicircular end sections are straightened, to facilitate insertion into the bone, and said length span may be increased to a desired value, wherein the plastic deformation strain $\delta$ for different ratios of R1/t does not exceed 15% in the fully martensitic phase, and wherein upon transformation to its austenitic shape, said staple generally resumes its original shape, but with a second length span that is greater than said first length span.

14. A method of bone fixation, which includes the steps of:

drilling at least one pair of bores across a fracture interface of a bone;

measuring the distance span between the two bores of the bore pair;

employing a staple for bone fixation, formed of a shape-memory alloy having a fully martensitic phase within a first temperature range, and having a fully austenitic phase within a second temperature range, which is higher than the first temperature range, which includes:

a web having a length span; and two semicircular end sections, having angles of curvature that are greater than 90°;

plastically deforming the staple, reversibly, in its martensitic phase, to simultaneously decrease said angle of curvature to 90°, thus straightening the semicircular end sections, to facilitate insertion into the bone, and to increase the length span of the web to a desired value;

inserting the staple into the bores; and employing the staple in a partially plastically deformed state, resulting from the length-span increase.

15. A method according to claim 14, wherein said step of plastically deforming the staple, reversibly, in its martensitic phase, includes plastically deforming the staple at a temperature range of the fully martensitic phase.

16. A method according to claim 14, wherein said step of plastically deforming the staple, reversibly, in its martensitic phase, includes plastically deforming the staple in a stress-induced martensitic phase at a temperature range of the fully austenitic phase.

17. A method according to claim 14, wherein said step of plastically deforming the staple further includes plastically deforming the staple to increase the length span to a value which is substantially the same value as the distance span between the two bores of the bore pair.

18. A method according to claim 14 wherein said step of plastically deforming includes plastically deforming to a strain that is less than 15%.

19. A method according to claim 14, wherein the staple is formed of a shape-memory alloy having a fully martensitic phase within a first temperature range, and having a fully austenitic phase within a second temperature range, which is higher than the first temperature range, and wherein said step of plastically deforming the staple includes plastically deforming the staple by reversible martensitic deformation.

20. A method according to claim 19, wherein said step of plastically deforming the staple by reversible martensitic deformation includes plastically deforming the staple at a temperature range of the fully martensitic phase.

21. A method according to claim 19, wherein said step of plastically deforming the staple by reversible martensitic deformation includes plastically deforming the staple in a stress-induced martensitic phase at a temperature range of the fully austenitic phase.

22. A method according to claim 19 wherein said step of plastically deforming includes plastically deforming to a strain that is less than 15%.

23. A system for increasing a length span of a staple, which includes:
   a) a staple formed of a shape memory alloy; and
   b) an apparatus for increasing a length span of a staple, wherein said apparatus includes:
      proximal and distal ends with respect to a user, which define a z-axis of an x;y;z coordinate system between them; and
      first and second prongs, joined by a system which provides a mechanical advantage to selectably bringing said first and second prongs together and pushing them apart,
      wherein said first prong further includes, at said distal end, a staple receptor, with a channel, for mounting said staple thereon, said channel defining an x-axis of the x;y;z coordinate system, parallel to said staple length span, and perpendicular to the direction of bringing first and second prongs together and pushing them apart,
      wherein said second prong further includes, at said distal end, a thin, cam-like head, having a width span that increases in the direction of increasing y, operable to increase said staple length span,
      and wherein, as said first and second prongs are brought together, said thin, cam-like head is arranged to slide between said staple receptor and said staple, mounted thereon, so as to wedge between said staple receptor and said staple and increase the length span of said staple.

24. System according to claim 23, wherein said staple has an initial length span of 6 mm, and wherein said apparatus is arranged for increasing said length span to a value between 6 and 10 mm.

25. System according to claim 23, wherein said staple has an initial length span of 10 mm, and wherein said apparatus is arranged for increasing said length span to a value between 10 and 14 mm.

26. System according to claim 23, wherein said staple has an initial length span of 14 mm, and wherein said apparatus is arranged for increasing said length span to a value between 14 and 18 mm.

27. System according to claim 23, wherein said staple has an initial length span between 3 and 100 mm, and wherein said apparatus is arranged for increasing said length span by an amount between 0 and 10 mm.

* * * * *